US010793592B2

(12) United States Patent
Skudas et al.

(10) Patent No.: US 10,793,592 B2
(45) Date of Patent: Oct. 6, 2020

(54) ACTIVATED CARBON FOR THE REMOVAL OF LEACHABLES AND/OR EXTRACTABLES

(71) Applicant: Merck Patent GmbH, Darmstadt (DE)

(72) Inventors: Romas Skudas, Mainz (DE); Klaus Adrian, Grosswallstadt (DE); Bianca Edlemann, Pfungstadt (DE); Sven Andrecht, Darmstadt (DE); Wilson Moya, Carlisle, MA (US)

(73) Assignee: Merck Patent GmbH, Darmstadt (DE)

( * ) Notice: Subject to any disclaimer, the term of this patent is extended or adjusted under 35 U.S.C. 154(b) by 251 days.

(21) Appl. No.: 15/524,824

(22) PCT Filed: Oct. 20, 2015

(86) PCT No.: PCT/EP2015/002071
§ 371 (c)(1),
(2) Date: May 5, 2017

(87) PCT Pub. No.: WO2016/070957
PCT Pub. Date: May 12, 2016

(65) Prior Publication Data
US 2017/0313741 A1 Nov. 2, 2017

(30) Foreign Application Priority Data
Nov. 6, 2014 (EP) .................................... 14003737

(51) Int. Cl.
| *C07K 1/22* | (2006.01) |
| *B01D 39/20* | (2006.01) |
| *B01D 15/00* | (2006.01) |
| *B01J 20/20* | (2006.01) |
| *B01D 15/38* | (2006.01) |
| *B01J 20/28* | (2006.01) |
| *B01J 20/30* | (2006.01) |
| *C07K 1/34* | (2006.01) |
| *C07K 1/36* | (2006.01) |
| *C07K 2/00* | (2006.01) |
| *C07K 16/00* | (2006.01) |

(52) U.S. Cl.
CPC ................ *C07K 1/22* (2013.01); *B01D 15/00* (2013.01); *B01D 15/3809* (2013.01); *B01D 39/2055* (2013.01); *B01J 20/20* (2013.01); *B01J 20/28004* (2013.01); *B01J 20/28016* (2013.01); *B01J 20/3078* (2013.01); *C07K 1/34* (2013.01); *C07K 1/36* (2013.01); *C07K 2/00* (2013.01); *C07K 16/00* (2013.01)

(58) Field of Classification Search
None
See application file for complete search history.

(56) References Cited

U.S. PATENT DOCUMENTS

| 5,104,530 A * | 4/1992 | Maroldo ................. B01J 20/20 210/198.2 |
| 5,543,096 A * | 8/1996 | Wu ........................ C04B 35/16 264/234 |
| 6,171,373 B1 * | 1/2001 | Park ...................... B01D 53/02 95/138 |
| 7,022,813 B2 | 4/2006 | Ayyagari et al. |
| 10,088,457 B2 | 10/2018 | Athenstaedt |
| 10,287,314 B2 | 5/2019 | Bian et al. |
| 2001/0009756 A1 | 7/2001 | Hei |
| 2002/0132971 A1 | 9/2002 | Ayyagari et al. |
| 2006/0093999 A1 | 5/2006 | Hei |
| 2006/0148645 A1 | 7/2006 | Schonfeld et al. |
| 2007/0253288 A1 | 11/2007 | Mennenga et al. |
| 2008/0171648 A1 | 7/2008 | Von Blucher et al. |
| 2009/0275121 A1 | 11/2009 | Greller et al. |
| 2010/0028990 A1 | 2/2010 | Broadley et al. |
| 2011/0003374 A1 | 1/2011 | Van Den Boogaard et al. |
| 2011/0058447 A1 | 3/2011 | Reif et al. |
| 2011/0058448 A1 | 3/2011 | Reif et al. |
| 2011/0207218 A1 | 8/2011 | Staheli et al. |
| 2011/0229517 A1 | 9/2011 | Strahlendorf et al. |
| 2012/0003733 A1 | 1/2012 | Gueneron |
| 2012/0149878 A1* | 6/2012 | Gillespie ................. C07K 1/18 530/387.3 |
| 2013/0197200 A1 | 8/2013 | Bian et al. |
| 2014/0046038 A1 | 2/2014 | Ishihara |

FOREIGN PATENT DOCUMENTS

| CN | 1376082 A | 10/2002 |
| CN | 102977182 A | 3/2013 |
| CN | 105324133 A | 2/2016 |
| DE | 20 2007 005 868 U1 | 7/2007 |

(Continued)

OTHER PUBLICATIONS

Zuo et al. "Removal of formaldehyde from overactivated-carbon-fiber-loaded biological enzyme" J. Appl Polym Sci 2013, pp. 29192623 (Year: 2013).*
Ahmed et al. "Enhanced toluene removal using granular activated carbon and a yeast strain Candida tropicalis in bubble-column bioreactors" J. of Hazardous Materials 176 (2010) 849-855 (Year: 2010).*
Bautista-Toledo et al. "Bisphenol A removal from water by activated carbon. Effects of carbon characteristics and solution chemistry" Environ. Sci. Technol. 2005, 39, 6246-6250 (Year: 2005).*

(Continued)

*Primary Examiner* — Daniel E Kolker
*Assistant Examiner* — James L Rogers
(74) *Attorney, Agent, or Firm* — Millen White Zelano & Branigan, PC

(57) ABSTRACT

The present invention relates to the purification of target molecules like recombinant and/or biotherapeutic proteins. Activated carbon can be used to remove leachables and/or extractables resulting from disposable equipment employed in the process.

20 Claims, 21 Drawing Sheets

(56) References Cited

FOREIGN PATENT DOCUMENTS

| WO | 99/34915 A1 | 7/1999 |
|----|----|----|
| WO | 01/23066 A1 | 4/2001 |
| WO | 2008/088379 A2 | 7/2008 |
| WO | 2011/079180 A1 | 6/2011 |
| WO | 2013/028330 A2 | 2/2013 |
| WO | 2014/004281 A1 | 1/2014 |

OTHER PUBLICATIONS

International Search Report dated Jan. 26, 2016, issued in corresponding PCT/EP2015/002071, 4 pages.
Ding, W., "Determination of Extractables and Leachables from Single-Use Systems", Chemie Ingenieur Technik, vol. 85, No. 1-2, 2013, pp. 186-196.
"Buffers, A guide for the preparation and use of buffers in biological systems", Calbiochem, 2003, 37 pages.
"BPSA, Recommendations for Extractables and Leachables Testing", BioProcess International, vol. 5, No. 11, Dec. 2007, pp. 36-49.
Shukla, A. et al., "Single-use disposable technologies for biopharmaceutical manufacturing", Trends in Biotechnology, vol. 21, No. 3, Mar. 2013, pp. 147-154.
Chen, J. et al., "Mesoporous Carbon Spheres: Synthesis, Characterization and Supercapacitance", International Journal of Elecrochemical Science, vol. 4, 2009, pp. 1063-1073.
Edmundson, I.C., "Particle-size Analysis", Advances in Pharmaceutical Sciences, vol. 2, 1967, pp. 95-174.
English translation Abstract of DE 20 2007 005 868 U1 published Jul. 19, 2007 (2 pages).
Cho : "Determination of total leachable bisphenol A from polysulfone membranes based on multiple consecutive extractions", Seungil Cho et al., <Talanta>>, vol. 101, p. 537-540.
Tachimoto : Applied technology of activated carbon: maintenance, management and existing problems>>, edited by Hideki Tachimoto, Southeast University Press, 1st edition, p. 157 successive table 4.2.11, p. 158 para.2.
First Office Action dated Nov. 20, 2019 in the corresponding China Examination Procedure 201580060422.0 (pp. 1-11).

* cited by examiner

Fig. 5 Part 1
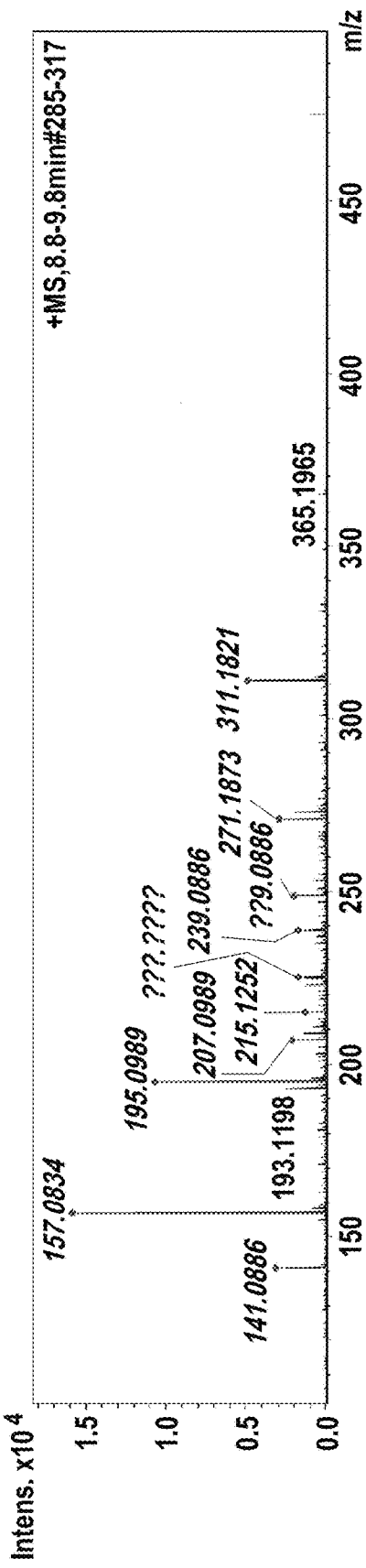
a) MS analysis of sample after single-use assembly
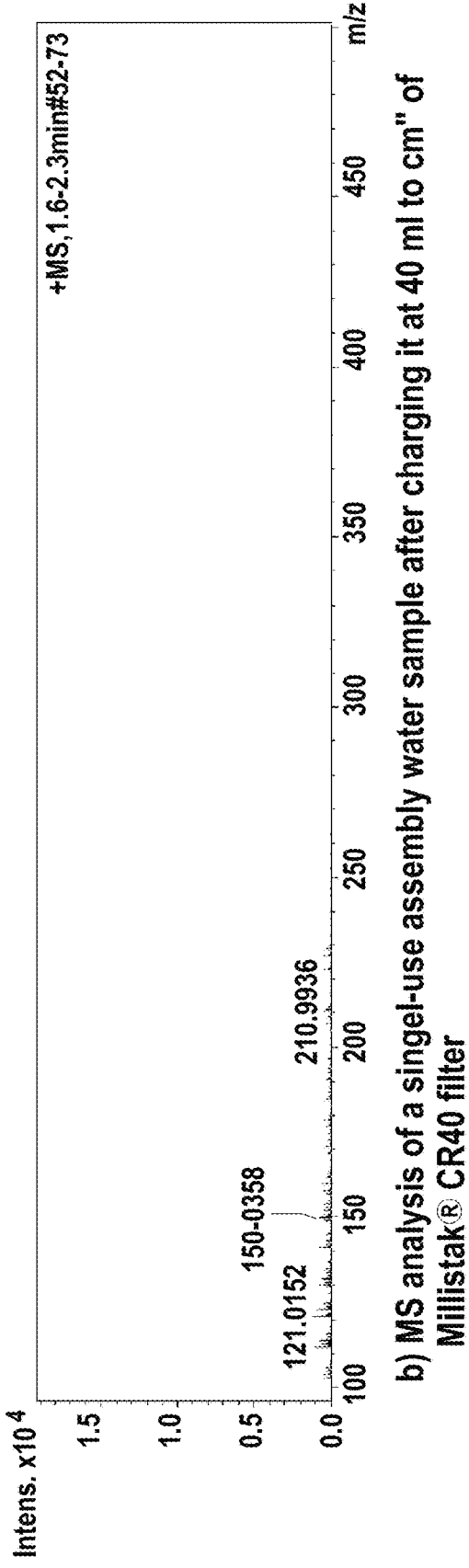
b) MS analysis of a singel-use assembly water sample after charging it at 40 ml to cm" of Millistak® CR40 filter

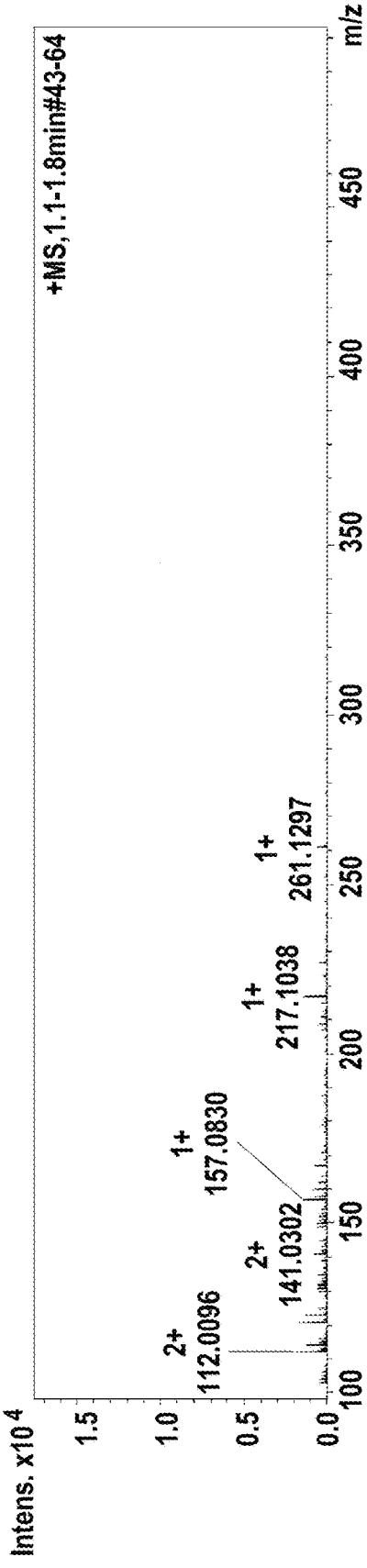
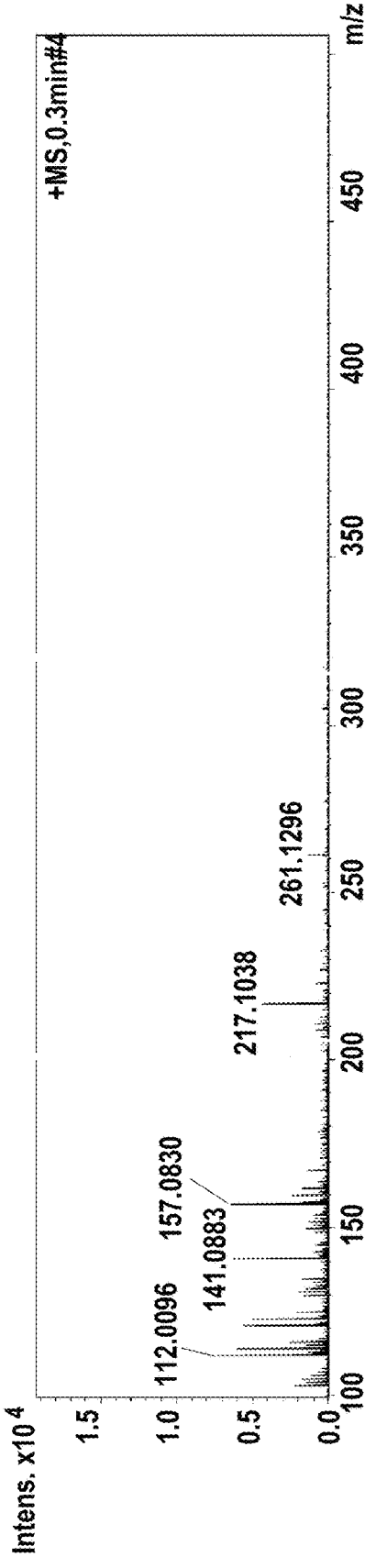
Fig. 5 Part 2

Fig. 6 Part 1
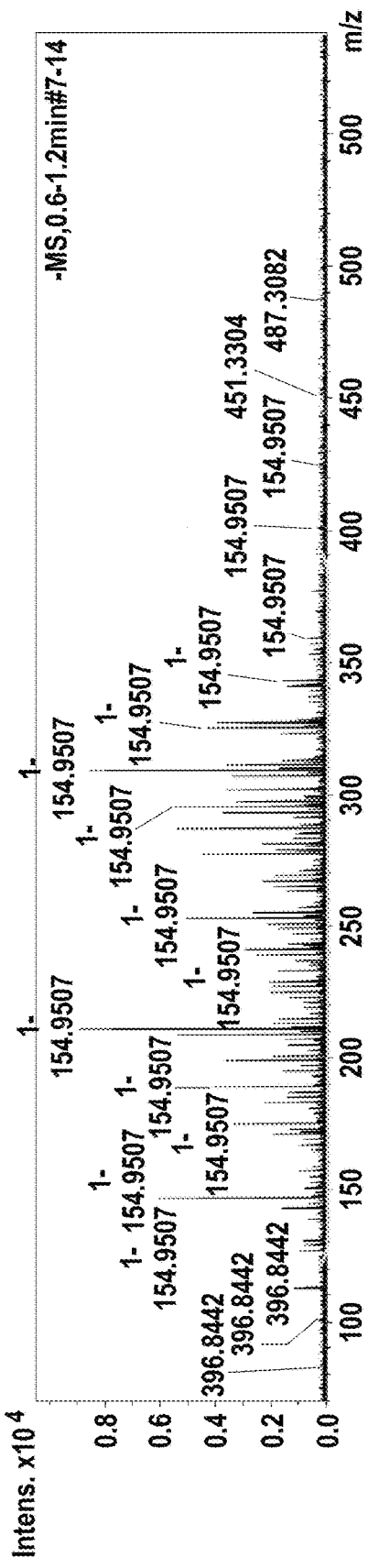
a) MS analysis of sample after single-use assembly
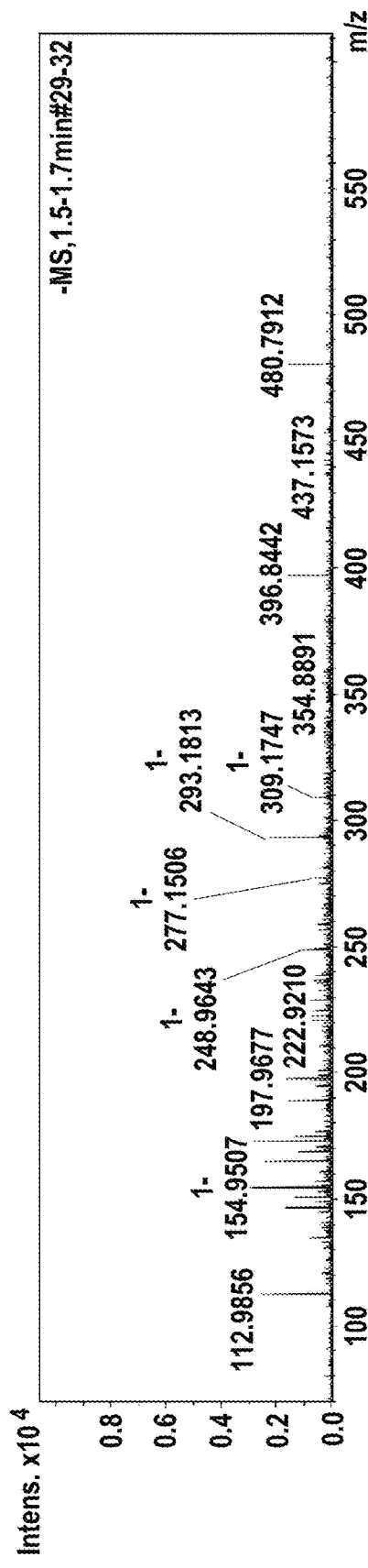
b) MS analysis of a singel-use assembly water sample after charging it at 40 ml to cm" of Millistak® CR40 filter

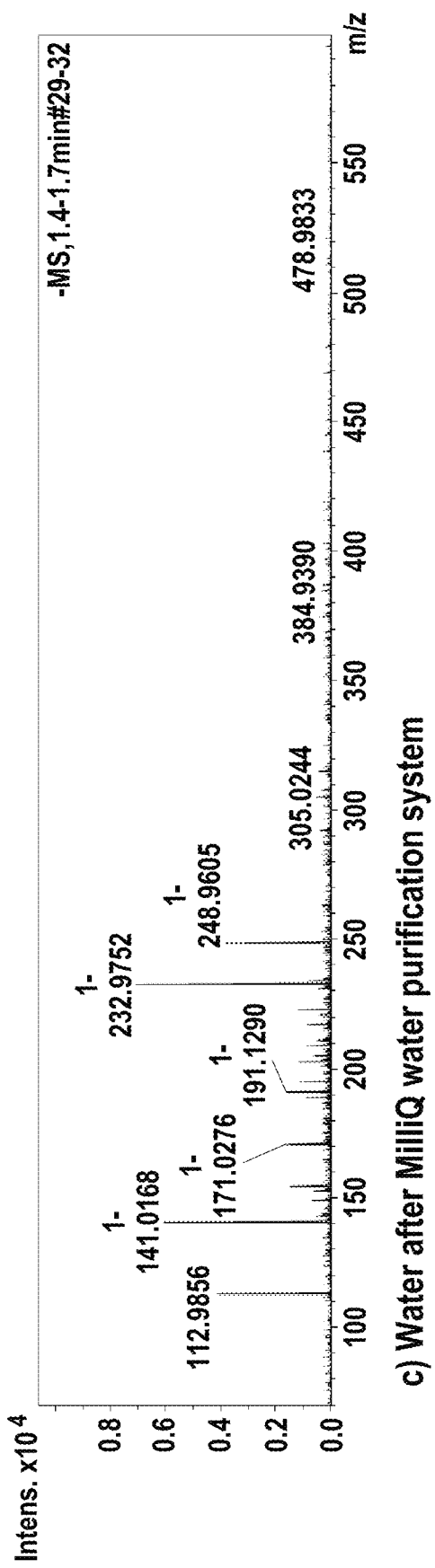
Fig. 6 Part 2

Fig. 7 Part 1
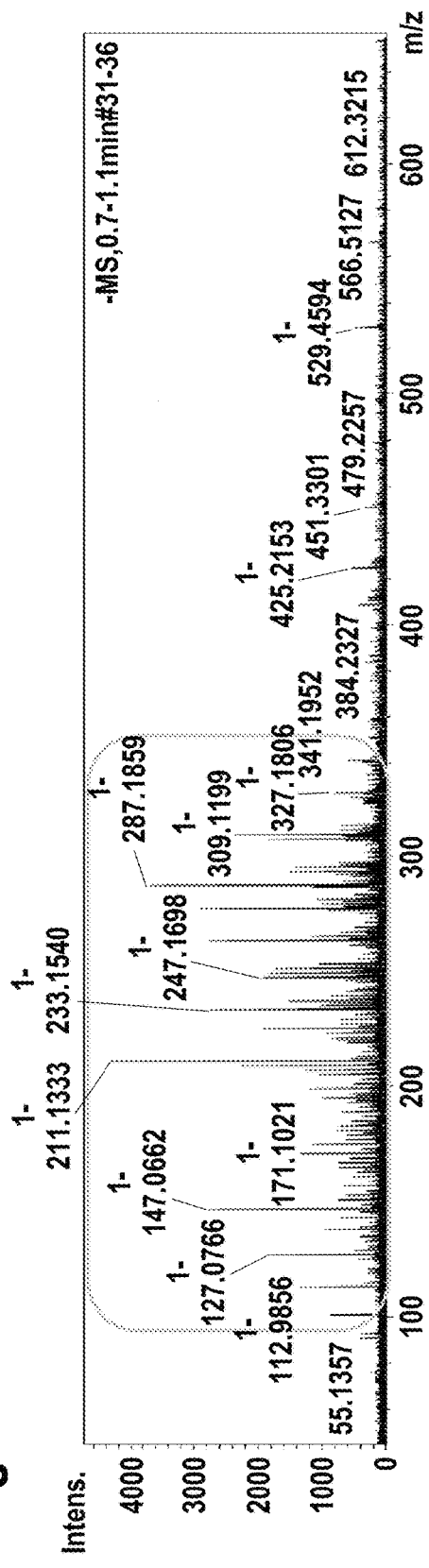
a) MS analysis of sample after single-use assembly
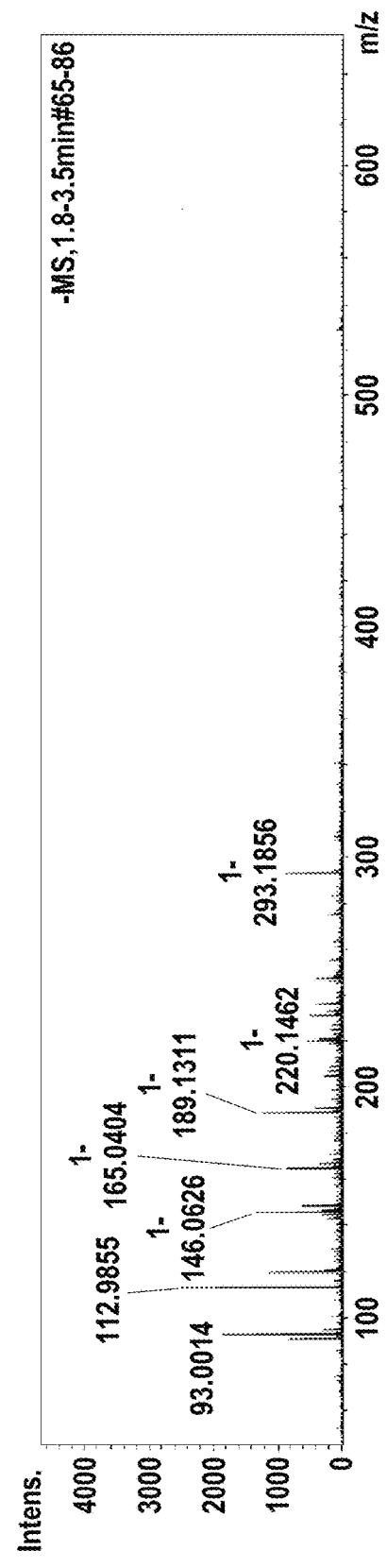
b) MS analysis of a singel-use assembly water sample after charging it at 40 ml to cm" of Millistak® CR40 filter

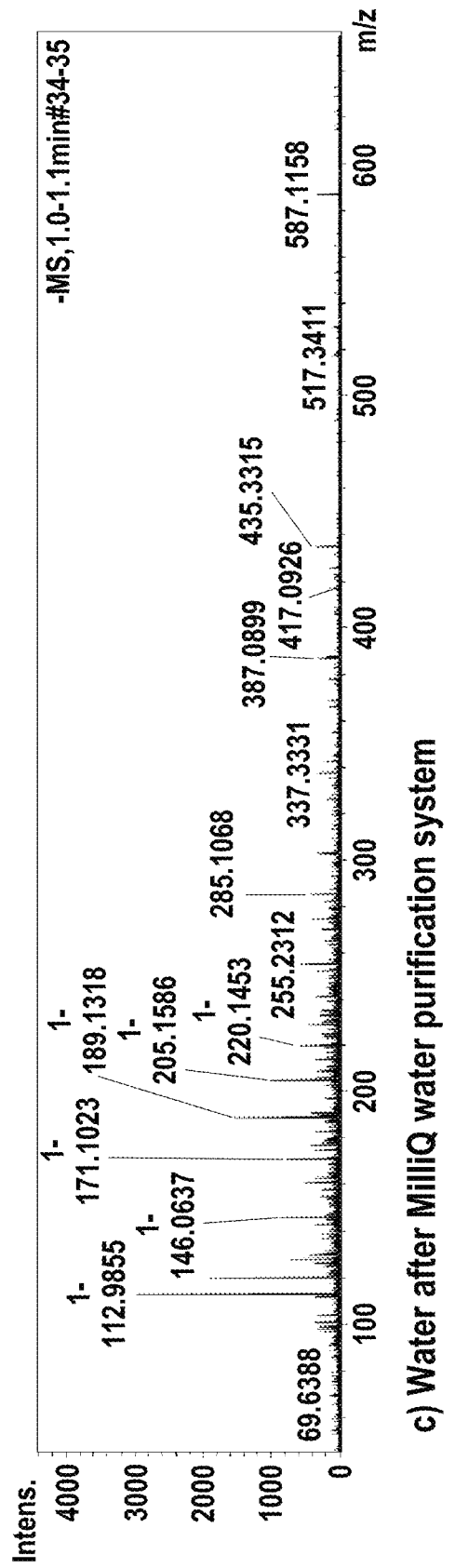
Fig. 7 Part 2
c) Water after MilliQ water purification system

Fig. 8 Part 1
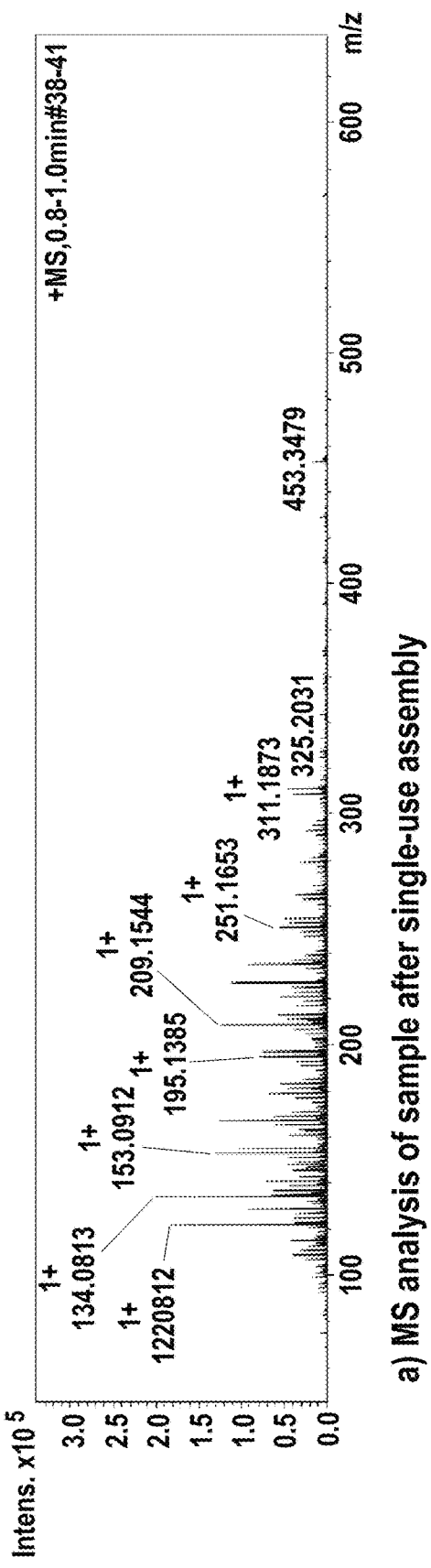
a) MS analysis of sample after single-use assembly
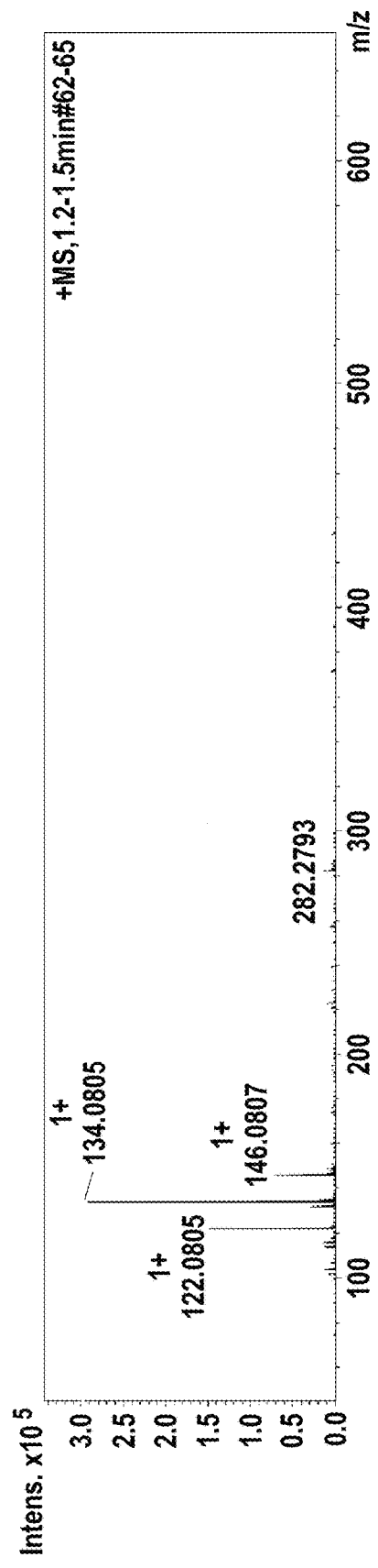
b) MS analysis of a singel-use assembly water sample after charging it at 40 ml to cm" of Millistak® CR40 filter

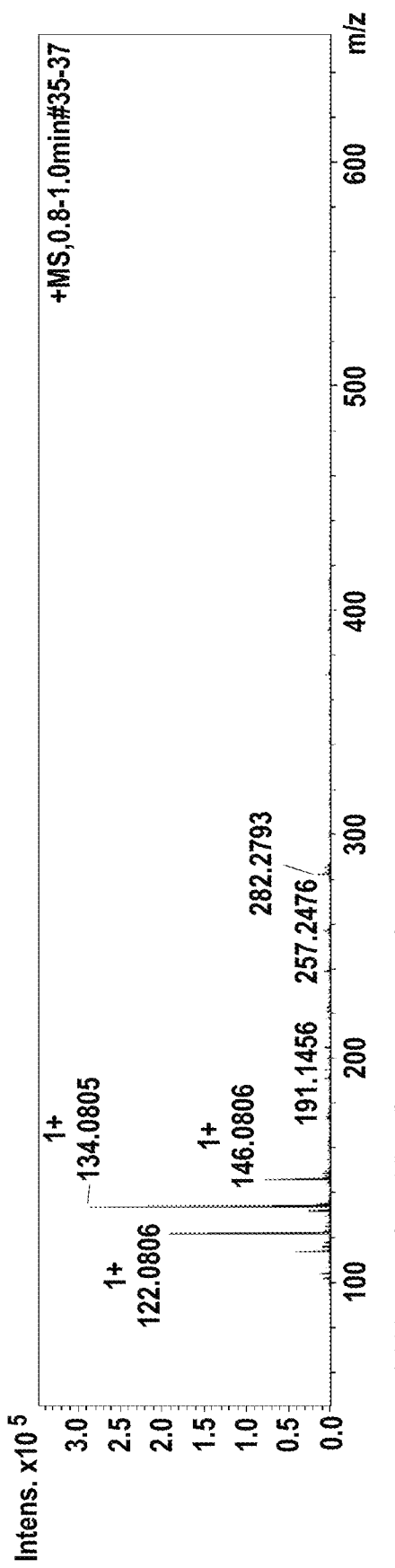

Fig. 10 Part 1
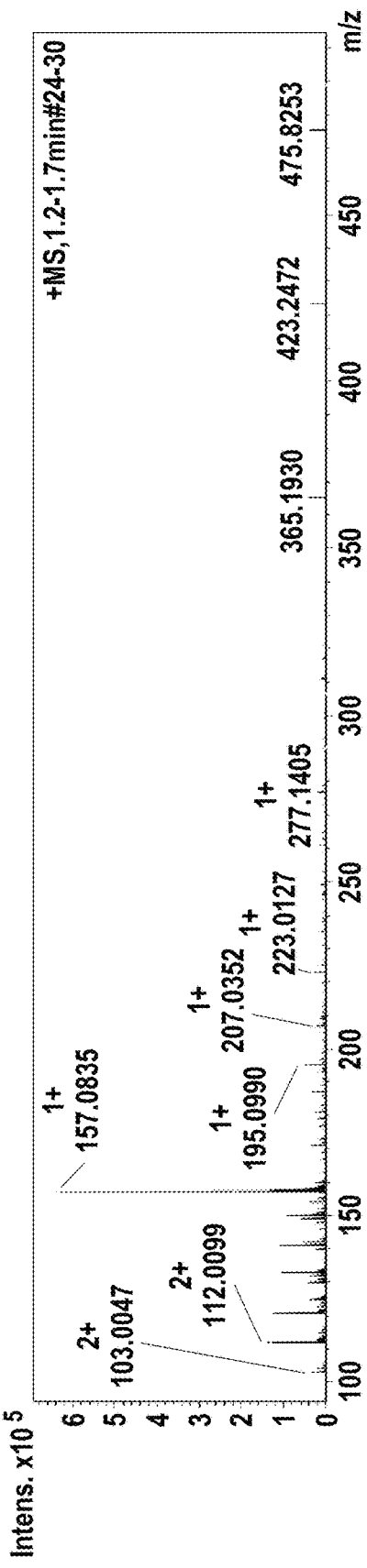
a) MS analysis of sample after single-use assembly
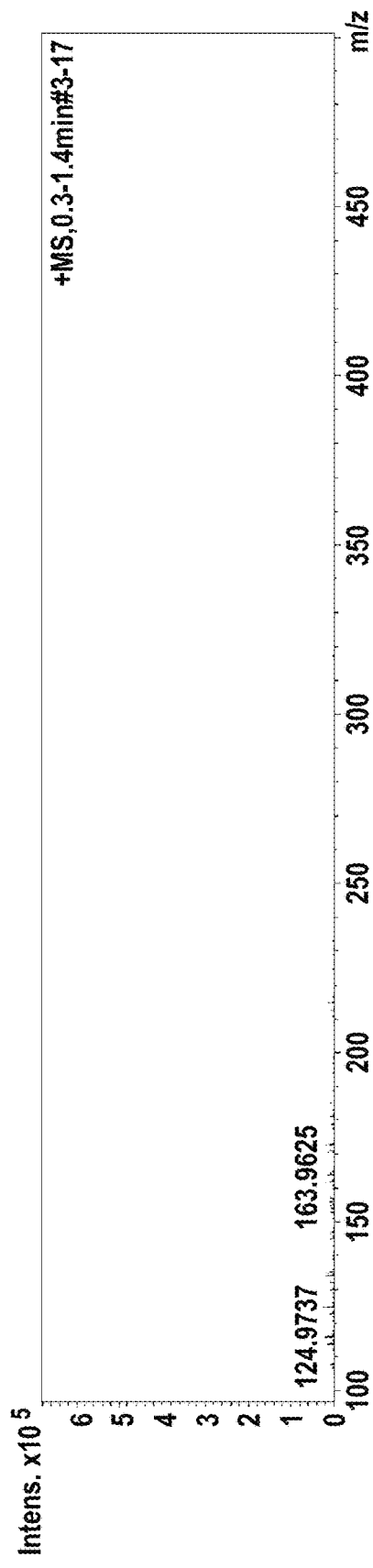
b) MS analysis of a singel-use assembly water sample after charging it at 40 ml to cm" of Millistak® CR40 filter

Fig. 10 Part 2
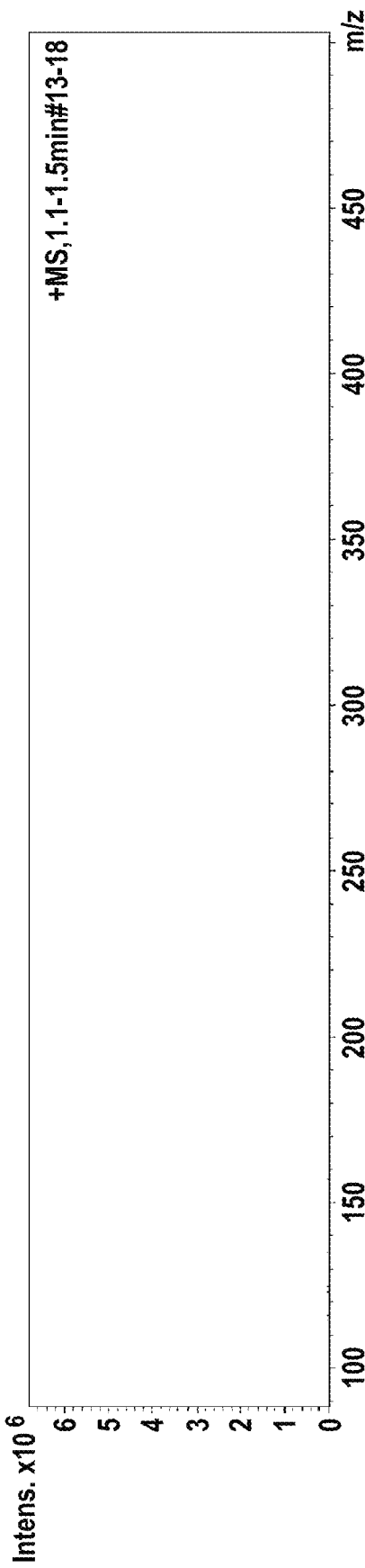
c) MS analysis of a singel-use assembly water sample after charging it at 80 ml to cm" of Millistak® CR40 filter
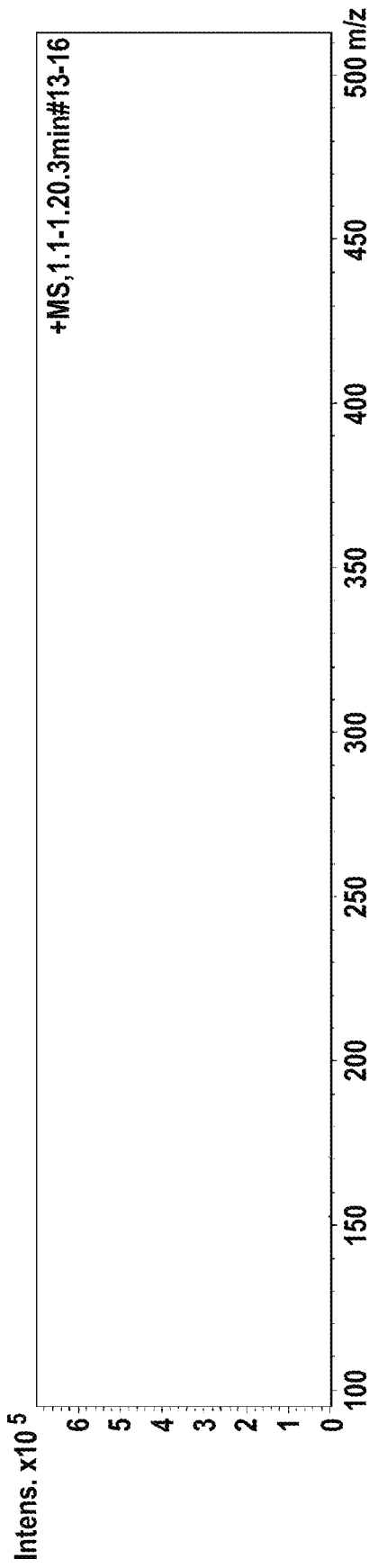
d) Water after MilliQ water purification system Fig. 11 Part 1
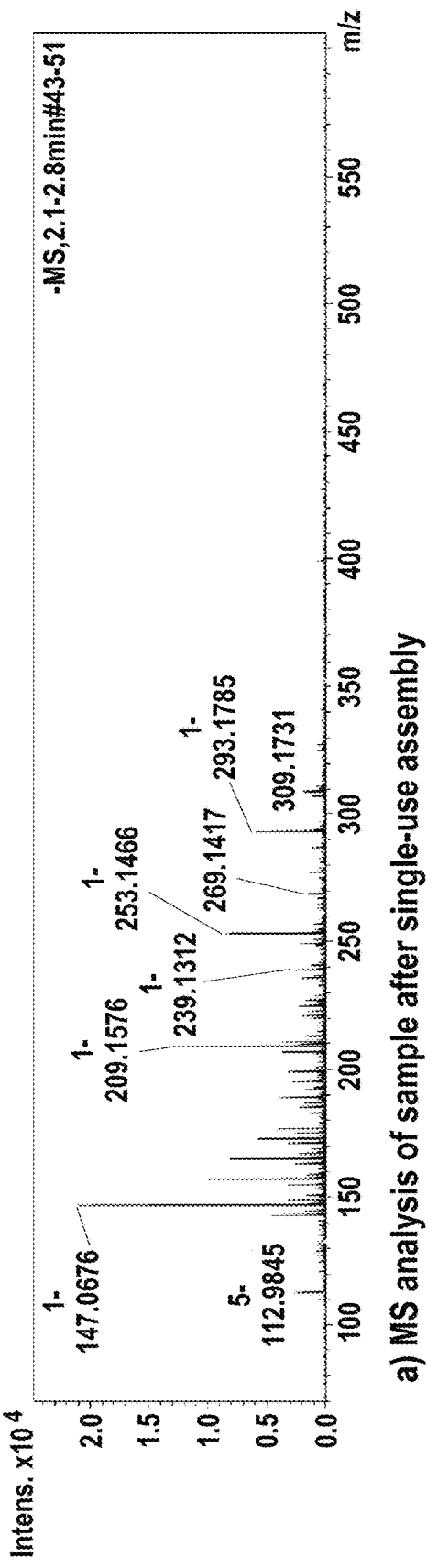
a) MS analysis of sample after single-use assembly
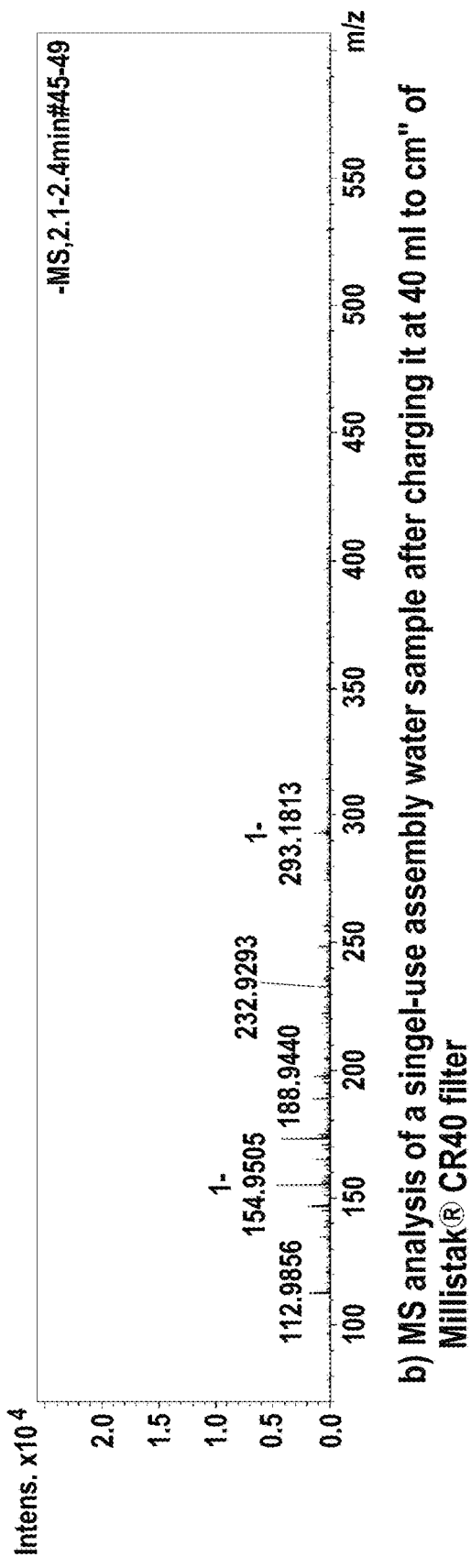
b) MS analysis of a singel-use assembly water sample after charging it at 40 ml to cm" of Millistak® CR40 filter

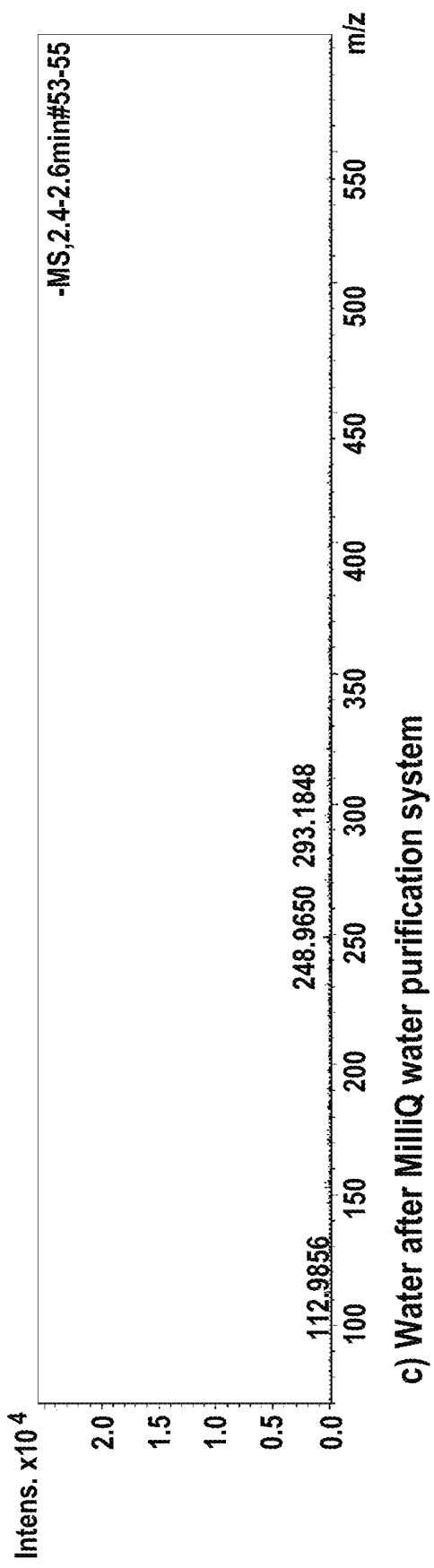
Fig. 11 Part 2
c) Water after MilliQ water purification system

Fig. 12 Part 1
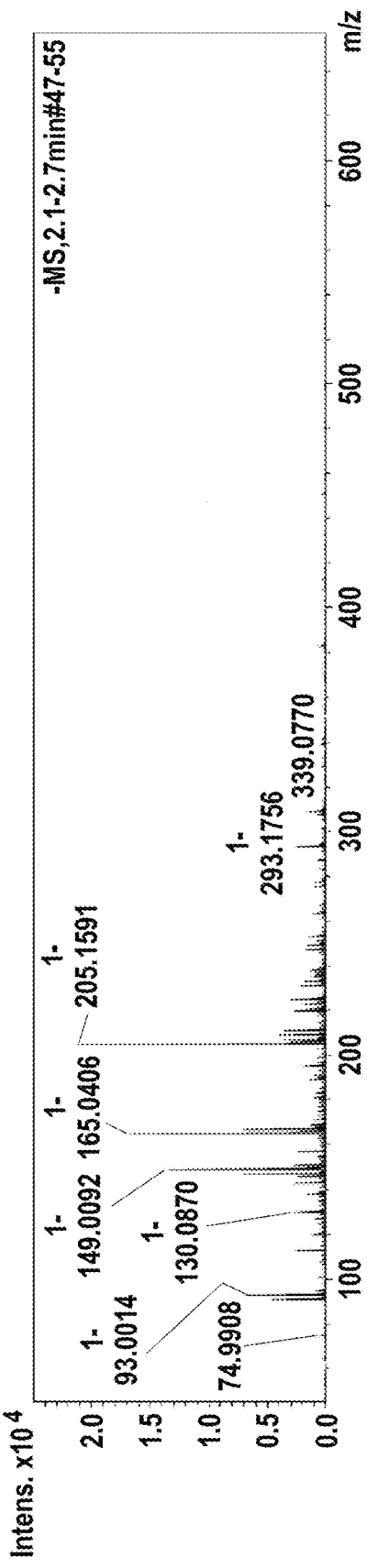
a) MS analysis of sample after single-use assembly
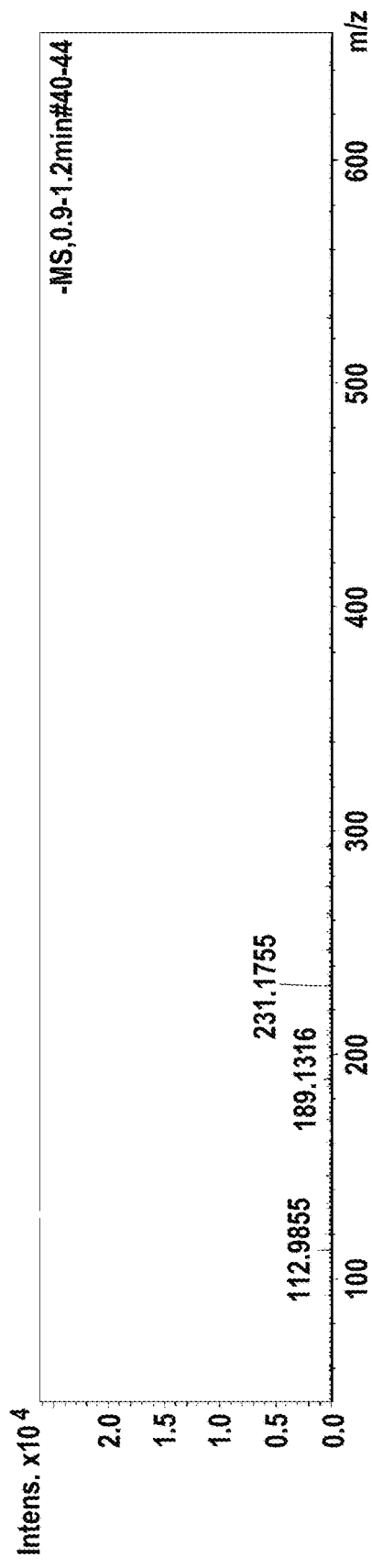
b) MS analysis of a singel-use assembly water sample after charging it at 40 ml to cm" of Millistak® CR40 filter

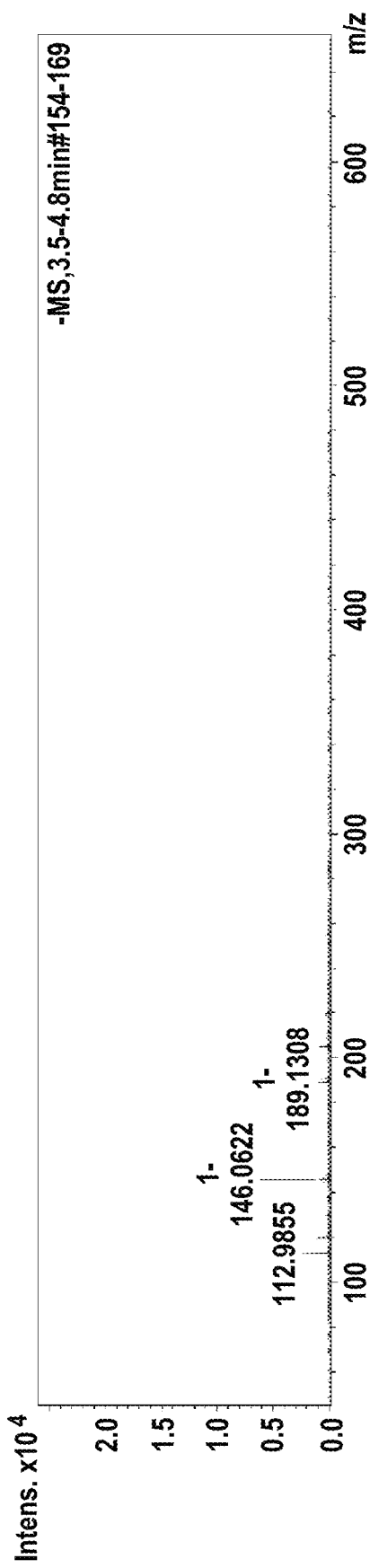
Fig. 12 Part 2

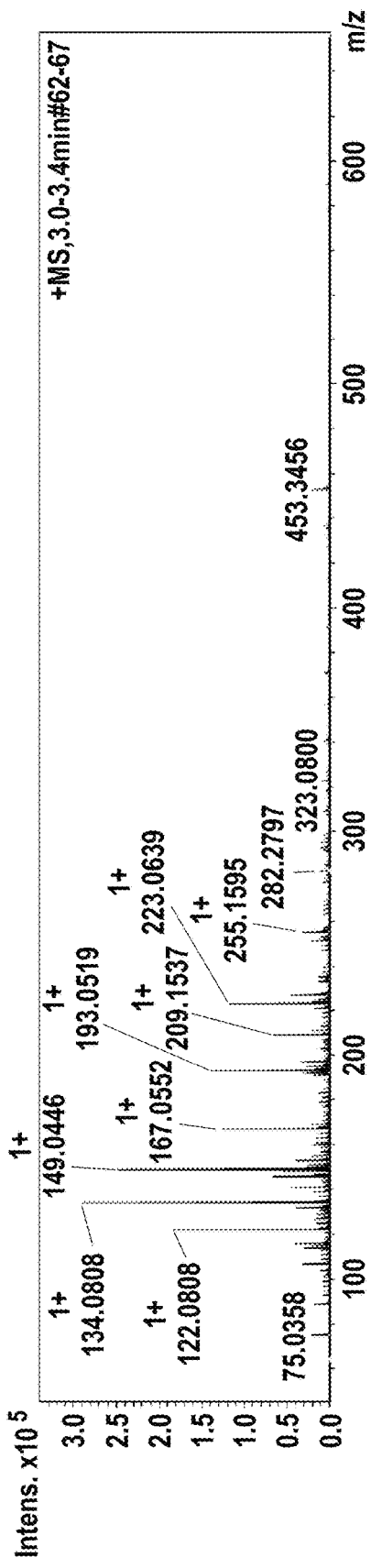
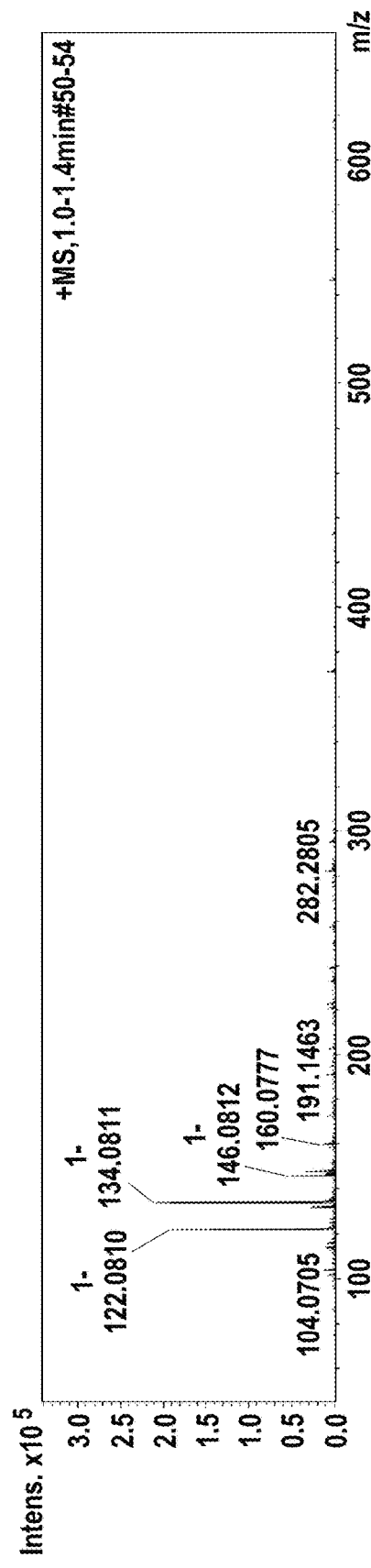
Fig. 13 Part 1
a) MS analysis of sample after single-use assembly
b) MS analysis of a singel-use assembly water sample after charging it at 40 ml to cm" of Millistak® CR40 filter

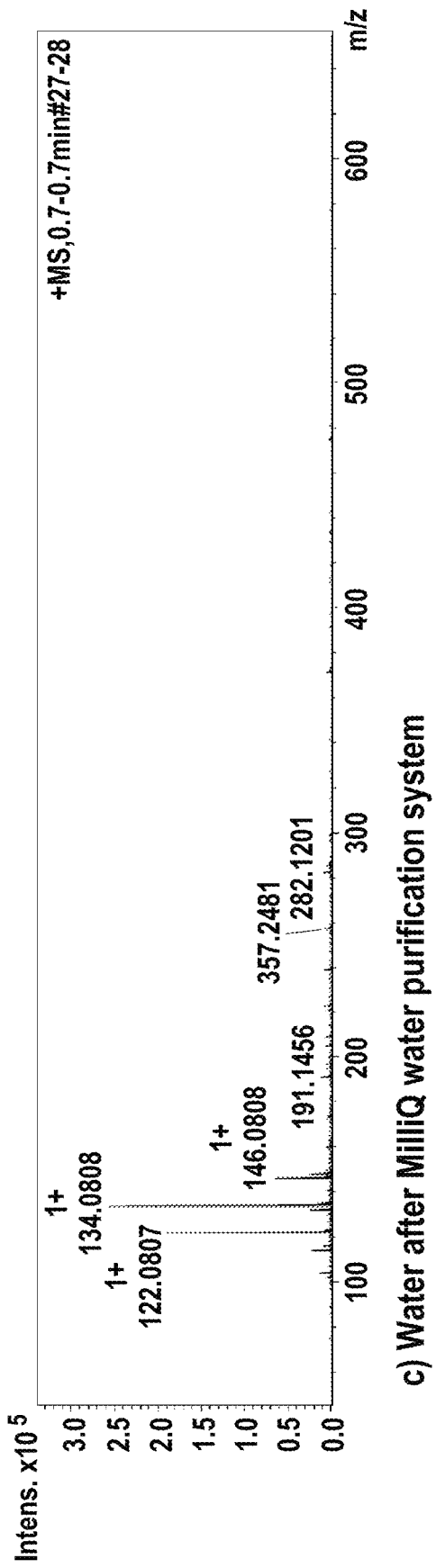

ACTIVATED CARBON FOR THE REMOVAL OF LEACHABLES AND/OR EXTRACTABLES

The present invention relates to the purification of target molecules like recombinant and/or biotherapeutic proteins, e.g. resulting from a cell expression system. Activated carbon can be used to remove leachables and/or extractables resulting from disposable equipment employed in the process.

BACKGROUND OF THE INVENTION

Efficient and economic large scale production of biomolecules, e.g., therapeutic proteins including antibodies, peptides or hormones, is an increasingly important consideration for the biotechnology and pharmaceutical industries. Generally, the purification processes are quite elaborate and expensive and include many different steps.

Typically, proteins are produced using cell culture methods, e.g. using either mammalian or bacterial cell lines recombinantly engineered to produce the protein of interest. In general, following the expression of the target protein, its separation from one or more impurities such as, e.g. host cell proteins, media components and nucleic acids, poses a formidable challenge. Such separation and purification is especially important if the therapeutic proteins are meant for use in humans and have to be approved by regulatory agencies, such as the Food and Drug Administration (FDA).

Conventional processes used today for the purification of proteins often include at least the following steps: (a) a clarification step for the removal of cells and cellular debris, e.g., using differential centrifugation and/or filtration; and (b) one or more downstream chromatography steps to separate the protein of interest from various impurities in the clarified cell culture feed.

Consequently, the production and purification of biomolecules is a multi-step procedure involving several types of purification media and also several types of equipment.

There is an emerging trend in biopharmaceutical industry to utilize single-use and/or disposable plastic materials for flexible, safe, reduced capital and operating cost manufacturing. Disposable bioprocessing equipment is available in wide range and scale from solution containers, transfer tubings to various devices. These equipment components come in direct contact with the product during the manufacturing process. It has been found that leachables and/or extractables from plastic material may end up in the finished product (W. Ding, Chemie Ingenieur Technik 2013, 85, No 1-2, 186-196). Though the level of leachables/extractables usually is below the one given in the guidance for industry (Q3C), there is a concern that even low levels of leachables/extractables could potentially affect drug product safety and influence performance leading to product safety and quality issues.

As a consequence, there is a need to remove leachables/extractables from the target biomolecule in bioprocesses to assure drug safety and quality while using disposable equipment.

BRIEF DESCRIPTION OF THE INVENTION

It has been found that the amount of leachables/extractables in the target molecule preparation resulting from the use of disposable equipment can be removed or reduced by filtration through activated carbon devices.

The present invention is thus directed to a method for purifying a target molecule whose production and/or purification process involves the use of disposable equipment whereby the target molecule is separated from leachables and/or extractables using activated carbon. Typically, the purification is performed by contacting the activated carbon with a liquid comprising the target molecule and potentially leachables and/or extractables, whereby the leachables and/or extractables when contacted with the activated carbon are kept or bound on the activated carbon and the liquid comprising the target molecule is not bound and is then separated from the activated carbon, e.g. by filtration.

In one embodiment the target molecule is a protein with a molecular weight of 10000 or more.

In one embodiment the target molecule is a glycoprotein.

In one embodiment the target molecule is an antibody.

In a preferred embodiment the leachables and/or extractables are one or more of the following components: Acetaldehyde, Toluene, 2-Hexanone, Acetone, 2-Butanone, Ethyl Acetate, Bisphenol A. Benzyl alcohol, Trimethyl Silanol, Formaldehyde, Bis (2-ethylhexyl) phthalate, 1-Methylethyl ester acetic acid, 2,4-di-t-butyl Phenol, 2-Octanone, 2-Pentanone, 3,3-dimethyl-2-Butanone, 3-ethoxy-Propane, 3-Hexanone, 3-Methoxy-1-butanol, Butanal, Cyclohexanone, Ethanol, Formic acid, Heptaethylene glycol, Hexanal, Methyl isobutyl ketone. Pentanal, t-Butanol, Tetrahydrofuran, Methyl formate.

In a preferred embodiment, the method is carried out at a pH between 3 to 9.

In another preferred embodiment the activated carbon is an activated carbon obtained by pyrolysis of an organic polymeric material, preferably polystyrene.

In a preferred embodiment, the activated carbon has a medium particle size between 5 and 40 μm.

In one embodiment, the target molecule is separated from leachables and/or extractables by filtration through one or more filters comprising activated carbon.

In one embodiment, the method of the present invention is used in a production and/or purification process comprising one or more of the following steps:
Cell culture in a bioreactor
Clarification
Purification
Filtration In another embodiment, in the method of the present invention, the target molecule is contacted with the activated carbon after a process step in which disposable equipment is used in combination with a temperature above 25° C. and/or mechanical deformation of the disposable equipment and/or in which the residence time of the target molecule in the disposable equipment is more than 1 hour.

The present invention is further directed to the use of activated carbon for the removal of leachables and/or extractables from liquids.

In a preferred embodiment, the liquid is contacted with the activated carbon in a filtration device, whereby the liquid flows through the filtration device comprising the activated carbon so that leachables and/or extractables are bound to the activated carbon while the liquid as well as target molecules comprised in the liquid are not bound to the activated carbon.

BRIEF DESCRIPTION OF THE DRAWINGS

FIG. 5 shows mass spectroscopy results using electrospray ionization (ESI+) method for the extractable/leachable detection after single-use assembly (Part 1) and after loading the processed water on the Millistak+® filter (Part 2).

FIG. 6 shows mass spectroscopy results using electrospray ionization (ESI−) method for the extractable/leachable detection after single-use assembly (Part 1) and after loading the processed water on the Millistak+® filter (Part 2).

FIG. 7 shows mass spectroscopy results using atmospheric pressure chemical ionization (APCI−) method for the extractable/leachable detection after single-use assembly (Part 1) and after loading the processed water on the Millistak+® filter (Part 2).

FIG. 8 shows mass spectroscopy results using atmospheric pressure chemical ionization (APCI−) method for the extractable/leachable detection after single-use assembly (Part 1) and after loading the processed water on the Millistak+® filter (Part 2).

FIG. 10 shows mass spectroscopy results using electrospray ionization (ESI+) method for the extractable/leachable detection after single-use assembly (Part 1) and after loading the processed water on the Millistak+® filter (Part 2).

FIG. 11 shows mass spectroscopy results using electrospray ionization (ESI−) method for the extractable/leachable detection after single-use assembly (Part 1) and after loading the processed water on the Millistak+® filter (Part 2).

FIG. 12 shows mass spectroscopy results using atmospheric pressure chemical ionization (APCI−) method for the extractable/leachable detection after single-use assembly (Part 1) and after loading the processed water on the Millistak+® filter (Part 2).

FIG. 13 shows mass spectroscopy results using atmospheric pressure chemical ionization (APCI−) method for the extractable/leachable detection after single-use assembly (Part 1) and after loading the processed water on the Millistak+® filter (Part 2).

Figure 1:
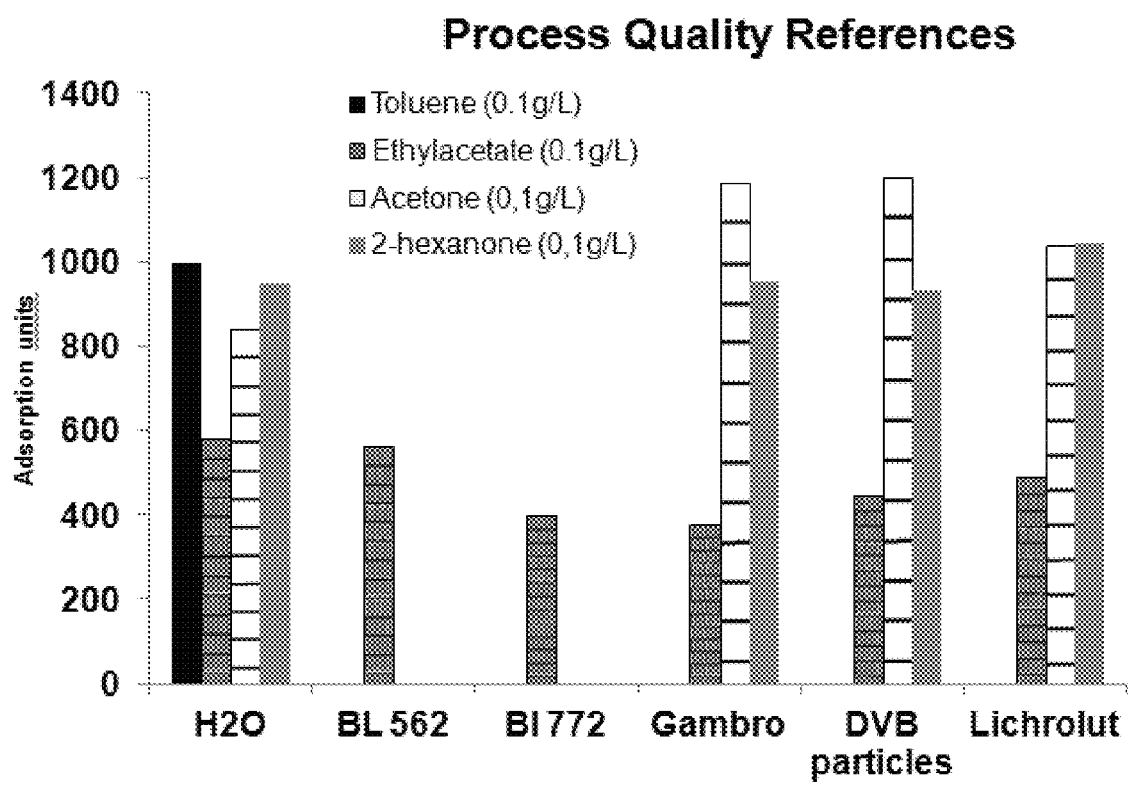
FIG. 1 shows adsorption of toxic and less toxic references on selected materials.

Further details concerning the Figures can be found in the Examples.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

As used herein the term "target molecule" refers to any molecule, substance or compound that shall be isolated, separated or purified from one or more other components, e.g. impurities, in a sample. Examples of target molecules are antibodies, fragment antigen binding (Fab), fragment constant region (Fc), proteins, peptides, recombinant proteins, other natural compounds, other biopharmaceutical compounds, vaccines or aggregates of biopharmaceutical compounds. In a preferred embodiment, the target molecule is a biomolecule, preferably a protein. In a very preferred embodiment, the target molecule is an antibody. In the production and/or purification process the target molecule is typically present in a liquid. The liquid might be water, a buffer, a non-aqueous solvent like ethanol or any mixture thereof. Beside the target molecule said liquid may comprise one or more impurities. The composition of the liquid may change during production and/or purification depending on the process steps that are performed. After a chromatographic step the liquid typically comprises other solvents than before because of the eluent used in the chromatographic step. Typically only after the very last step purification step the target molecule might be dried for preparing the final dosage form.

The term "antibody" refers to a protein which has the ability to specifically bind to an antigen. Typically, antibodies are having a basic four-polypeptide chain structure consisting of two heavy and two light chains, said chains being stabilized, for example, by interchain disulfide bonds. Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins. According to the present invention fusion proteins are also encompassed by the term "antibody".

In some embodiments, an antibody is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CDI Ia, CDI Ib, CDI Ic, CD 18, an ICAM, VLA-4 and VCAM; a tumor associated antigen such as HER2, HER3 or HER4 receptor; and fragments and/or variants of any of the above-listed polypeptides. In addition, an antibody according to the present invention is any protein or polypeptide, fragment or variant thereof, that binds specifically to any of the above-listed polypeptides.

As used herein, and unless stated otherwise, the term "sample" refers to any composition or mixture that contains a target molecule. Samples may be derived from biological or other sources. Biological sources include eukaryotic and prokaryotic sources, such as plant and animal cells, tissues and organs. Preferred samples are from cell culture fluid like mammalian cell culture, e.g. CHO, NS-0, SP2/0, BioWa, bacterial cell culture, e.g. *E. coli, B. subtilis*, yeast cell culture, or filamentous fungi. The sample may also include diluents, buffers, detergents, and contaminating species, debris and the like that are found mixed with the target molecule. The sample may be "partially purified" (i.e., having been subjected to one or more purification steps, such as filtration steps) or may be obtained directly from a host cell or organism producing the target molecule (e.g., the sample may comprise harvested cell culture fluid).

The term "impurity" or "contaminant" as used herein, refers to any foreign or objectionable molecule, including a biological macromolecule such as DNA, RNA, one or more host cell proteins, nucleic acids, endotoxins, lipids, impurities of synthetic origin and one or more additives which may be present in a sample containing the target molecule that is being separated from one or more of the foreign or objectionable molecules. Additionally, such impurity may include any reagent which is used in a step of the production and/or purification process. Leachables and/or extractables are also impurities.

The terms "purifying," "separating," or "isolating," as used interchangeably herein, refer to increasing the degree of purity of a target molecule by separating it from a composition or sample comprising the target molecule and one or more other components, e.g. impurities. Typically, the degree of purity of the target molecule is increased by removing (completely or partially) at least one impurity from the composition.

The term "chromatography" refers to any kind of technique which separates an analyte of interest (e.g. a target molecule) from other molecules present in a mixture. Usually, the target molecule is separated from other molecules as a result of differences in rates at which the individual molecules of the mixture migrate through a stationary medium under the influence of a moving phase, or in bind and elute processes. Examples for chromatographic separation processes are reversed phase chromatography, ion exchange chromatography, size exclusion chromatography, affinity chromatography, hydrophobic interaction chromatography and mixed mode chromatography.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

"Disposable equipment" or "single-use equipment" is a product designed for a limited number of uses after which it is recycled or is disposed as solid waste or, preferably, a product designed for a single use, e.g. the use in the purification of one batch of raw material resulting from a bioreactor. The term often implies cheapness and short-term convenience rather than medium to long-term durability. The term is also sometimes used for products that may last several weeks or months (e.g. disposable filters) to distinguish from similar products that last indefinitely (e.g. washable filters). Preferably, a "single use equipment" is an equipment that is only used a single time, whereby the duration of the use is defined by the duration of the process in which it is used, e.g. a filtration process, a bioreactor process etc.

Disposable equipment is made of plastic materials like polyamides, polycarbonates, polymethylpentene, polystyrene, polyethylene, polyesters, polyvinyls like polyvinylchloride, polysulfones like polyethersulfones, polytetrafluoroethylene, celluloseacetate, ethylvinylacetate or polypropylene. Disposable equipment can be any equipment needed in the production and purification of a target molecule, e.g. bioreactors, pool tanks, surge tanks, surge bags, any types of tubings, valves, columns, filters, cartridges or connectors, The term "bioreactor," as used herein, refers to any manufactured or engineered device or system that supports a biologically active environment. In some instances, a bioreactor is a vessel in which a cell culture process is carried out which involves organisms or biochemically active substances derived from such organisms. Such a process may be either aerobic or anaerobic. Commonly used bioreactors are typically cylindrical, ranging in size from liters to cubic meters, and are often made of stainless steel. In some embodiments described herein, a bioreactor might contain a disposable constituent made of a material other than steel and is disposable. In some embodiments that is a disposable bag where in the biologically active environment is maintained. It is contemplated that the total volume of a bioreactor may be any volume ranging from 100 mL to up to 10,000 Liters or more, depending on a particular process. Disposable or single use bioreactors provide an alternative to reusable bioreactors and are used to carry out preferably one biological or biotechnological process before being disposed of. By providing a new disposable bioreactor for each process, and one that is preferably sterilized during the production process, it is possible to reduce the risk of (cross-) contamination, while simultaneously obviating the need to perform and document the impeccable cleaning and sterilization of a previously used bioreactor. Disposable bioreactors are often designed as flexible containers, for example as bags, or as containers having walls that are flexible in sections thereof at least. Examples of such bioreactors are described in US 2011/0003374 A1, US2011/0058447A1, DE 20 2007 005 868U1, US 2011/0058448A1, US2011/0207218A1, WO 2008/088379A2, US 2012/0003733 A1, WO2011/079180 A1, US2007/0253288A1, US 2009/0275121 A1 and US 2010/0028990A1.

As used herein, the term "pool tank" refers to any container, vessel, reservoir, tank or bag, which is generally used between process steps and has a size/volume to enable collection of the entire volume of output from a process step. Pool tanks may be used for holding or storing or manipulating solution conditions of the entire volume of output from a process step.

In some embodiments, the processes and systems for the production and purification of a target molecule may use one or more pool tanks or surge tanks throughout the process.

The term "surge tank" as used herein refers to any container or vessel or bag, which is used between process steps or within a process step (e.g., when a single process step comprises more than one step); where the output from one step flows through the surge tank onto the next step. Accordingly, a surge tank is different from a pool tank, in that it is not intended to hold or collect the entire volume of output from a step; but instead enables continuous flow of output from one step to the next.

The terms "clarify," "clarification," and "clarification step," as used herein, refers to a process step for removing suspended particles and or colloids, thereby to reduce turbidity, of a target molecule containing solution, as measured in NTU (nephelometric turbidity units). Clarification can be achieved by a variety of means, including centrifugation or filtration.

Centrifugation could be done in a batch or continuous mode, while filtration could be done in a normal flow (e.g. depth filtration) or tangential flow mode. In processes used in the industry today, centrifugation is typically followed by depth filters intended to remove insoluble impurities, which may not have been removed by centrifugation. Furthermore, methods for enhancing clarification efficiency can be used, e.g. precipitation.

Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation. The terms "depth filter" or "depth filtration" as used herein refer to a filter that is capable of retaining particulate matter throughout the filter medium, rather than just on the filter surface. In some embodiments described herein, one or more depth filters are used in the clarification process step.

The term "leachable and/or extractables" as used herein means impurities that can be found in the target molecule preparation or the liquid comprising the target molecule during and after the production and/or purification process, whereby said impurities result from the equipment, especially the disposable equipment, employed in the production and purification process. Extractables are chemical compounds that migrate from any material which is in direct contact with the target molecule into the target molecule or the liquid comprising the target molecule when exposed to an appropriate solvent under certain conditions of time, temperature and mechanical force. Materials which might emit extractables include elastomeric, plastic or coating components.

Leachables are chemical compounds, typically a subset of extractables, that migrate into the target molecule preparation from any target molecule-contact material, including elastomeric, plastic or coating components as a result of direct contact with the target molecule preparation or the liquid comprising the target molecule under normal process conditions or accelerated storage conditions and are found in the liquid comprising the target molecule and if not removed also in the final target molecule product.

Typically, extractables tests are performed using a model solvent whereas leachables studies use the actual target molecule or process fluid.

Typically, extractables are obtained under exaggerated or aggressive conditions but leachables tests use normal process conditions.

Consequently, typically, leachables are shown as a subset of extractables. In some cases, due to the interaction of process fluid or target molecule with process equipment, some leachable compounds are not part of the extractables.

Details about extractables and leachables can be found in BPSA Extractables and Leachables Subcommittee, *BioProcess Int* 2007, 5 (11), 36.

Examples of leachables and/or extractables are Acetaldehyde, Toluene, 2-Hexanone, Acetone, 2-Butanone, Ethyl Acetate, Bisphenol A, Benzyl alcohol, Trimethyl Silanol, Formaldehyde, Bis (2-ethylhexyl) phthalate, 1-Methylethyl ester acetic acid, 2,4-di-t-butyl Phenol, 2-Octanone, 2-Pentanone, 3,3-dimethyl-2-Butanone, 3-ethoxy-Propane, 3-Hexanone, 3-Methoxy-1-butanol, Butanal, Cyclohexanone, Ethanol, formic acid, Heptaethylene glycol, Hexanal, Methyl isobutyl ketone, Pentanal, t-Butanol, Tetrahydrofuran, Methyl formate.

The state-of-the art biopharmaceutical production process typically uses genetically modified cells to express the target of interest in the bioreactor following by numerous unit operations to purify it. For some of the biopharmaceutical molecules, such as monoclonal antibodies, platform processes are being used consisting of centrifugation, depth filtration, chromatographic purification, virus inactivation, chromatographic polishing, virus filtration and ultrafiltration/diafiltration steps to obtain bulk drug substance. A biopharmaceutical molecule purification process is established to remove potentially contaminating and harmful agents, such as bacteria, viruses, host cell proteins and host cell DNA, target molecule scaffolds or aggregates, purification process leachables and extractables (Shukla, A. A., Gottschalk U, Trends in Biotechnology, March 2013, Vol. 31, No. 3, 147-154).

DETAILED DESCRIPTION OF THE INVENTION

The gist of the present invention is the finding that activated carbon, especially activated carbon obtained by the pyrolysis of an organic polymeric material can be used to remove leachables and/or extractables resulting from the use of disposable equipment. It is known from WO201404281 and US 2014/046038 that activated carbon can generally be used in biopharma production processes to remove impurities. But it had not been found out yet that activated carbon is especially suitable for the removal of leachables and/or extractables resulting from the use of disposable equipment.

Activated carbon is a material having extensive non-specific adsorption properties, and is used as an adsorbent or as a decolorant in the industrial fields, such as the production of chemicals and foods, sewage or waste water treatment, water filtration, and production of small-molecule drugs. The term "active carbon" or "activated carbon" as used interchangeably herein, refers to a carbonaceous material which has been subjected to a process to enhance its pore structure. Activated carbons are porous solids with very high surface areas. They can be derived from a variety of sources including coal, wood, coconut husk, nutshells, peat and also organic polymers. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

It has been found that activated carbon that has been obtained from organic polymers is especially effective in removing leachables and/or extractables according to the present invention. Organic polymers are any synthetic, chemically defined organic polymers, like e.g. polystyrene, polyamide, polycarbonate, polymethylpentene, polyethylene, polyesters, polyvinyls or polypropylene.

Preferably, the activated carbon comprises or preferably consist of spherical active carbon particles. That means they have essentially similar extensions in all three spatial dimensions. Besides the spherical shape, cubical, parallelepiped or cylindrical shapes are imaginable, provided that the extensions in two different spatial dimensions do not differ by more than a factor 3, preferably less than a factor 2.

The activated carbon obtained from organic polymers can be produced by pyrolysis of spherical organic material, for example polystyrene. However, it is also possible to pyrolyze glucose solutions, as described in Int. J. Electrochem. Sci., Vol. 4, 2009, pages 1063 to 1073. The manufacture of spherical activated carbon is further disclosed in US 20060148645 and US 2008171648.

An exemplary way of manufacturing such active carbon polymer particles is to use polymer balls, in particular ion exchanger balls, the polymer structure of which contains separable functional groups, in particular sulfonyl groups and/or carboxyl groups, as an educt. The porous polymer balls are pyrolyzed, and optionally the pyrolyzed polymer balls are subjected to an activation step. The separation of the functional groups preferably occurs up to a residual content (referred to the weight share of the functional groups, as used) of 5% to 15%. The temperature of this first heat treatment is suitably in the range from 200° C. to 350° C. for 10 min to 60 min. The atmosphere is in principle arbitrary. The following pyrolysis step starts at a temperature, which essentially corresponds to the final temperature of the first heat treatment, and preferably ends at 600° C. to 800° C. The heating-up rate is suitably in the range from 5 K/min to 0.5 K/min, and therefrom the duration of the pyrolysis step can immediately be calculated. The activation step is uncritical and occurs in a conventional way.

Suitable spherical activated carbons are also available as SARATECH™ 100562, SARATECH™ 100772 and SARATECH™ 101373 (Blücher GmbH, Erkrath, Germany).

The activated carbon has a surface area of preferably 10 to 10000 $m^2/g$, more preferably of 100 to 5000 $m^2/g$, most preferably of 1000 to 2000 $m^2/g$.

The mean particle size of the activated carbon is preferably at least 2 μm, more preferably from 2 to 550 μm and very particularly from 5 to 40 μm.

Characterization of particles is known in the art and preferably made by sieving. this is described by: I. C. Edmundson, Particle-size analysis, H. S. Bean, A. H. Beckett and J. E. Caries (eds) in: Advances in Pharmaceutical Sciences vol. 2, Academic Press, London 1967, 95-174.

The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of activated carbon having a certain particle size range, e.g. of 5 to 40 μm, is preferably at least 90% by weight, more preferably at least 95% by weight, most preferably at least 98% by weight of the whole activated carbon.

The type and amount of leachables and/or extractables that can be found in the production and/or purification process of a target molecule depends on several aspects, like the equipment used in the process as well as the conditions like temperature, solvents, pH under which the process is run. Typical leachables and/or extractables are Acetaldehyde, Toluene, 2-Hexanone, Acetone, 2-Butanone, Ethyl Acetate, Bisphenol A, Benzyl alcohol, Trimethyl Silanol, Formaldehyde, Bis (2-ethylhexyl) phthalate, 1-Methylethyl ester acetic acid, 2,4-di-t-butyl Phenol, 2-Octanone, 2-Pentanone, 3,3-dimethyl-2-Butanone, 3-ethoxy-Propane, 3-Hexanone, 3-Methoxy-1-butanol, Butanal, Cyclohexanone, Ethanol, formic acid, Heptaethylene glycol, Hexanal, Methyl isobutyl ketone, Pentanal, t-Butanol, Tetrahydrofuran. Methyl formate. Especially Toluene, 2-Hexanone, Acetone, 2-Butanone, Ethyl Acetate, Bisphenol A, Benzylalcohol, Trimethylsilanol, Formaldehyde and Bis (2-ethylhexyl) phthalate have been identified as leachables and/or extractables of importance. Toluene, 2-Hexanone, Acetone, 2-Butanone and Ethyl Acetate have proven to be suitable reference compounds to monitor and reference the process quality and the amount of residual leachables and/or extractables.

To perform the method of the present invention, at any stage of the production and/or purification process of the target molecule, the target molecule which is typically present in a liquid is contacted with activated carbon. This should of course take place after a process step in which a disposable equipment has been employed. Biopharma production typically comprises several process steps like cell culture in a bioreactor, clarification, chromatography, viral clearance, filtration etc. Each of these steps as well as the preparation of media and buffers to be used in these steps can involve the use of disposable equipment. Disposable equipment can be employed once or several times within the production and/or purification process. The use of activated carbon can be performed once or several times in a production and/or purification process. It can be performed as additional process step or can be included in an existing process step, e.g. a filtration step.

In one embodiment, the target molecule which is typically present in a liquid is contacted with activated carbon after a process step in which disposable equipment is used in combination with one or more of the following process features:
- elevated temperature—this means that in this process step during contact of the product solution with the disposable equipment, the temperature is at least partly above 25° C. This is e.g. the case with disposable bioreactors in which cells are typically cultured at 37° C.
- long exposure time—this means that in this process step the contact of the product solution with the disposable equipment is for more than 1 hour. This is e.g. the case in disposable bioreactors in which cells are typically cultured for several days or in process steps like chromatography steps in which the chromatographic separation takes more than 1 hour so that the solution comprising the target molecule is stored in disposable tanks for more than 1 hour.
- Mechanical deformation—this means that a disposable equipment is mechanically deformed or is treated with mechanical force, e.g. when using a hose pump or when a plastic bag is pressed together to release the liquid contained therein. Such deformation typically increases the release of leachables and/or extractables from the plastic material.

In another embodiment, the target molecule which is typically present in a liquid is contacted with activated carbon two times or more in the process.

The contact with the activated carbon can be performed by mixing the liquid containing the target molecule with the activated carbon and afterwards separating the liquid from the activated carbon e.g. by sedimentation, centrifugation and/or preferably filtration. The contact time between the activated carbon and the liquid is typically between 5 and 30 minutes.

In a preferred embodiment, the contacting is performed by flowing the liquid containing the target molecule through the activated carbon. For this the activated carbon might be packed in a column, a cartridge, a filter or any other suitable device. Typically, the residence time of the liquid in the device is between 0.5 and 5 min. A person skilled in the art is able to adapt the flow rates to achieve the suitable residence time as well as the amount of liquid and activated carbon.

The liquid comprising the target molecule is typically the liquid resulting from the process step after which the method of the invention shall be performed. It can be water, a buffer, an organic liquid or any mixture thereof. Typically it is an aqueous buffer. The liquid typically comprises the target molecule as well as one or more impurities like leachables and/or extractables.

The removal of leachables and/or extractables with activated carbon may be performed under a broad range of extraction conditions, like pH, conductivity and ionic strength. Typically the solution containing the target molecule can be directly applied to the activated carbon without changing pH, conductivity and ionic strength of the solution. The pH of the liquid containing the target molecule can for example be between pH 3 and 9 when contacting the activated carbon. The presence of an organic solvent in the solution might nevertheless influence the binding capacity of the activated carbon.

The extraction of leachables and/or extractables with activated carbon is based on adsorptive size exclusion, which means that the leachables and/or extractables are bound in the pores of the activated carbon while the target molecule is too big to enter the pores and can thus not be bound within the pores. While the target molecule can thus be recovered in the non-adsorption fraction, the leachables and/or extractables are adsorbed onto the activated carbon, thereby reducing the amount of leachables and/or extractables in the liquid comprising the target molecule.

The amount of activated carbon to be used for the method of the invention depends on the amount and/or origin of leachables and/or extractables that might be present. For 0.005 g of leachables and/or extractables typically at least 1 g of activated carbon is suitable. Typically 1 g of activated carbon can be used for 0.0001 to 0.005 g of leachables and/or extractables, preferably for 0.0005 to 0.0015 g of leachables and/or extractables. It has been found that for toluene, aceton, bisphenol the amount of activated carbon that is needed for their removal from the solution comprising the target molecule is lower than the amount needed to effectively remove aldehydes. Preferably at least 1 g of activated carbon or most preferred about 1 g of activated carbon is used for about 0.001 g of leachable and/or extractables such as toluene, aceton, bisphenol and about 0.0005 g of leachable and/or extractables such as acetaldehyde.

It has been found that activated carbon obtained from organic polymers is especially suitable for the removal of leachables and/or extractables. The most efficient reduction of leachables and/or extractables can be reached with this type of material.

It has further been found that activated carbon with a relatively small particle size of between 4 and 50 μm is especially suitable for the method of the present invention.

The method of the present invention for the first time provides an easy and effective way to remove leachables and/or extractables from a target molecule. Activated carbon is a material known in the art that can be easily included in the purification process without taking the risk of adding new contaminants to the target molecule.

The method of the invention is suitable to remove at least 50%, preferably at least 75%, most preferred at least 90% of the leachables and/or extractables from a target molecule. It has been found that the method of the invention is especially suited to remove leachables and/or extractables such as ketones, alcohols, aromatic hydrocarbons like toluene and benzylalcohol from the target molecule. It is to be expected to remove 90% of above named leachables and/or extractables using appropriate device scaling.

The entire disclosures of all applications, patents, and publications cited above and below, especially corresponding European patent application EP 14003737.5 filed Nov. 6, 2014, are hereby incorporated by reference.

Examples

Static Binding of Leachables and/or Extractables Using Activated Carbon Materials For the following experiment commercially available materials (e.g. Activated Carbon 100772, Blücher GmbH, Erkrath, Germany ("BL772"); Activated Carbon 100562, Blücher GmbH, Erkrath, Germany ("BL562"); Activated Carbon from Adsorba® 150C hemoperfusion cartridge, Gambro Dialysatoren GmbH, Hechingen, Germany ("Gambro"); LiChrolut® EN (40-120 μm), Merck KGaA, Darmstadt, Germany ("Lichrolut"); Polyspher PST 10, Merck KGaA, Darmstadt, Germany ("DVB particles") were dried in a vacuum oven for 24 h at 40° C. and then 1 gram of dried material was weighed in a glass flask. Then 15 ml of water with dissolved test molecule 0.1 g/L was given to the glass flask. The glass flask was then subjected to shaker for 15 minutes. After shaking, the glass flasks were centrifuged for 15 minutes at 4000 rotations/min. The solution was then filtered and subjected to headspace GC-MS. The given values are an average value from 3 measurements (FIG. 1-2).

Activated carbon materials ("BL 562" and "BL 772") could adsorb 3 out of 4 selected reference materials under the limit of detection.

Activated carbon materials ("BL 562" and "BL 772") could adsorb 2 out of 3 selected reference materials under the limit of detection and reduce the amount of acetaldehyde appr. 3 times.

Figure 2:
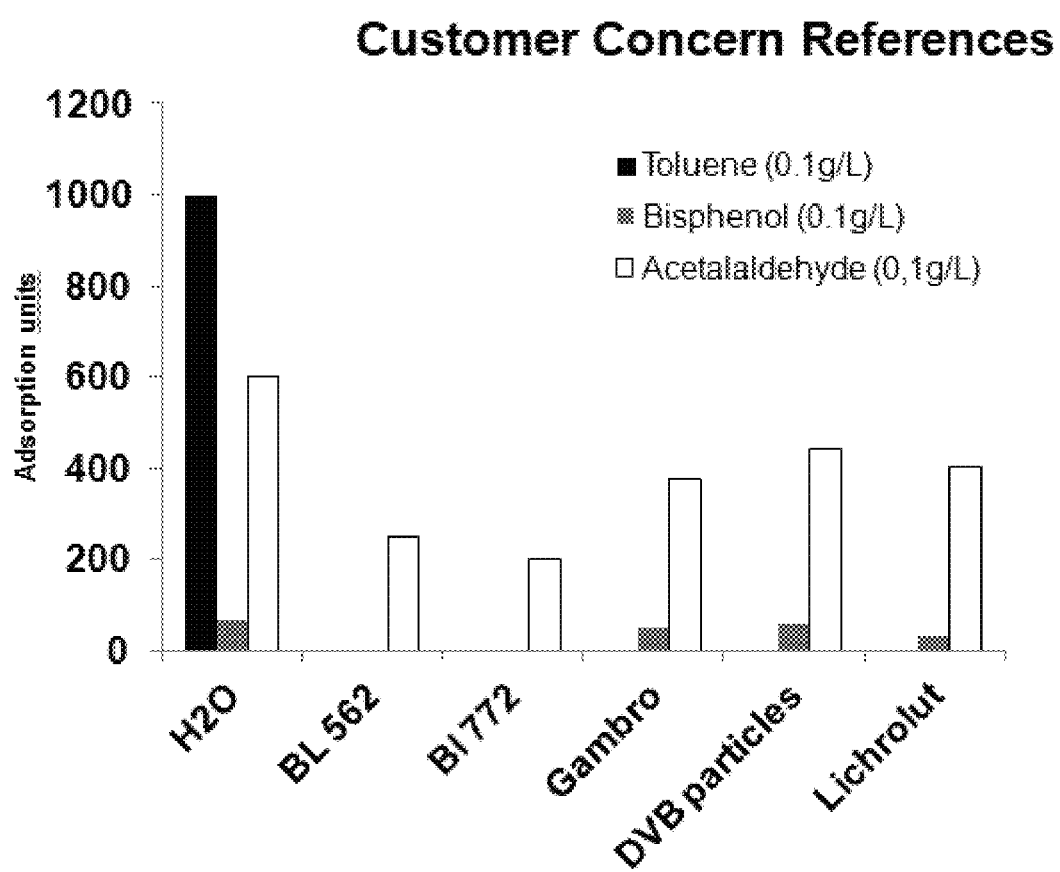
FIG. 2 shows adsorption of selected references on various materials.
Figure 3:
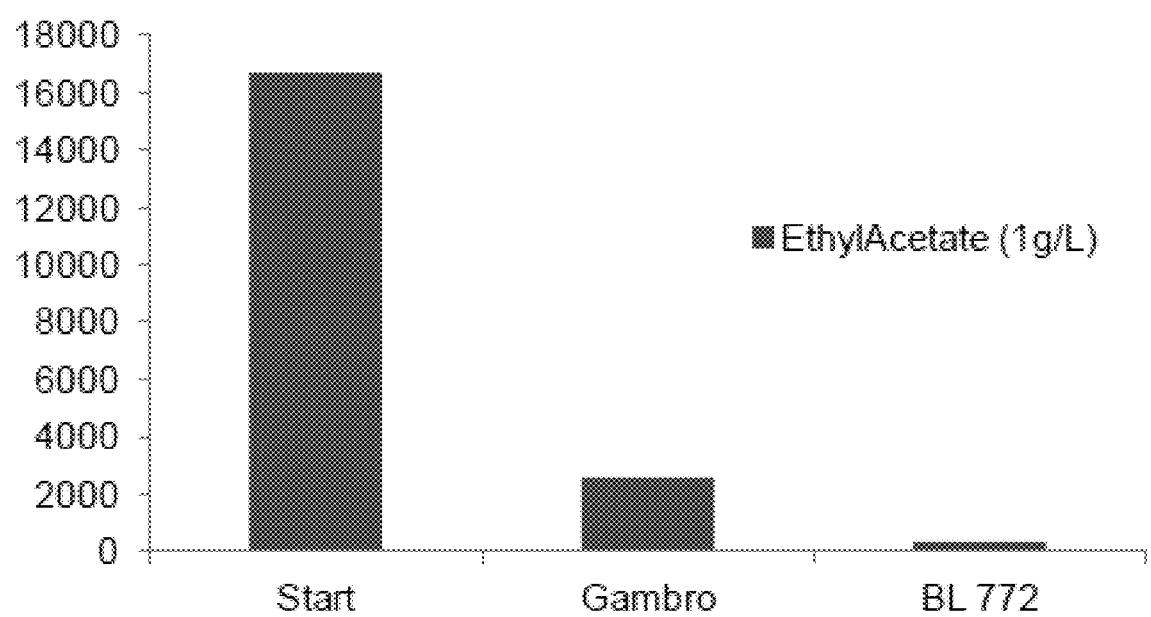
FIG. 3 shows adsorption of ethylacetate on selected activated carbon materials.

Additionally, increased levels of ethylacetate (1 g/L) were used to estimate the adsorption capability of activated carbon excluding the detection error (FIG. 1). The experimental set up was the same as described above, but the concentration of ethylacetate was increased to 1 g/L and 2 activated carbon materials were used ("BI 772" and "Gambro") (FIG. 3). The achieved results confirm that "BL 772" can be successfully used to adsorb ethylacetate from model solutions.

Application of Activated Carbon and Millistak+CR40 Filters for the Single-Use Bioprocessing Assemblies (Mobius Virus Clearance Assembly)

For the following example single-use assembly was tested with pure water: Mobius® Disposable Assembly (Gamma Irradiated (min 25-40 kGy; MS0010L30EP, EMD Millipore Corporation, Billerica, Mass., USA) of 10 L solution bag was connected with Lynx ST connector (STC21THN01, EMD Millipore Corporation, Billerica, Mass., USA) to tubing (Pharma 50, 7486040801 PU-6, EMD Millipore Corporation, Billerica, Mass., USA) following by female lure (5621000821, EMD Millipore Corporation, Billerica, Mass., USA) connection to Mobius® Disposable Assembly (Gamma Irradiated (min 25-40 kGy; MS0010L30EP, EMD Millipore Corporation, Billerica, Mass., USA) of 10 L solution bag;

The assembly was installed in a Mobius® Virus Clearance unit (EMD Millipore Corporation, Billerica, Mass., USA) and 10 L of pure water was flown through using unit's peristaltic pump at 1.5 L/hour flow rate. The processed water was gathered in the Mobius® Disposable Assembly 10 L solution bag at room temperature.

Figure 4:
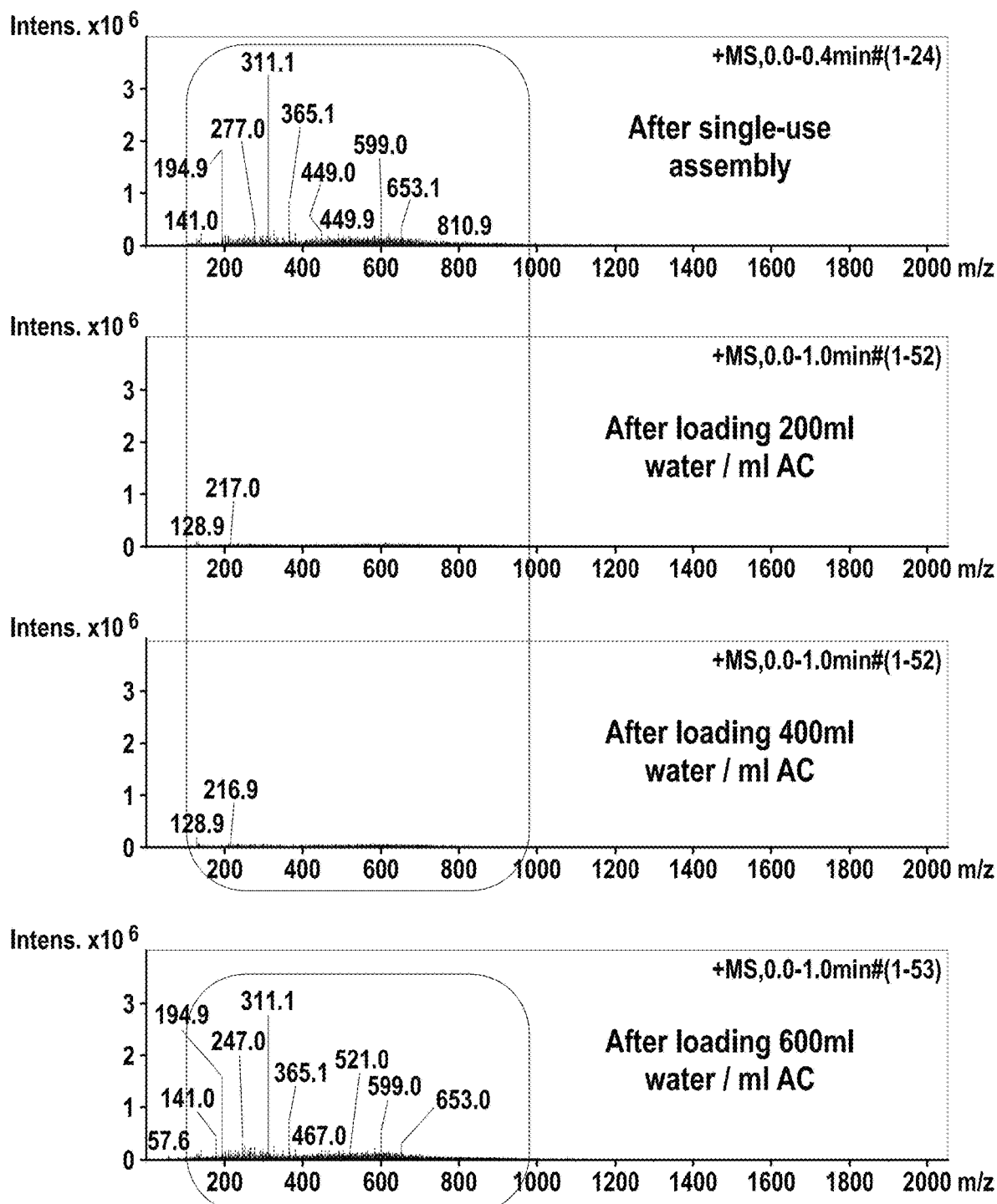
FIG. 4 shows mass spectroscopy results using electrospray ionization (ESI+) method for the extractable/leachable detection after single-use assembly and after loading the processed water on the glass column packed with activated carbon.

Then the 10 L water containing bag was connected to a equilibrated Superformance® glass column (10*150 mm, Götec Labortechnik, Bickenbach, Germany) packed with activated carbon (100772, Blücher GmbH, Erkrath) and operated at 4 ml/min using peristaltic pump. The flow through water was gathered in separate glass containers and subjected to FIA-MS (flow injection mass spectrometry at 200 µl/min Bruker Esquire 3000+, Bruker Corporation, Billerica, Mass., USA) using electrospray ionization (ESI+) method. The results are given in FIG. 4.

Filtration of single-use assembly processed water through glass column packed with activated carbon reduced the level of extractable/leachable (according FIA-MS-ESI+ method) to <ppm range, showing very sharp break through profile.

Additionally, the 10 L processed water containing bag was connected to an equilibrated Millistak+® media in uPOD™ format CR40 23 cm² (EMD Millipore Corporation, Billerica, Mass., USA) containing activated carbon and operated at 4 ml/min using peristaltic pump. The flow through water was gathered in separate glass containers and subjected to FIA-MS (flow injection mass spectrometry at 200 µl/min Bruker Esquire 3000+, Bruker Corporation, Billerica, Mass., USA) using electrospray ionization (ESI+, ESI−) and atmospheric pressure chemical ionization (APCI−, APCI+) methods. The results are given in FIG. 5-FIG. 8.

Filtration of single-use assembly processed water through Millistak+® CR40 filter reduced the level of extractable/leachable (according FIA-MS-ESI+; ESI− method) by intensity of 10×.

Filtration of single-use assembly processed water through Millistak+® CR40 filter reduced the level of extractable/leachable (according FIA-MS-APCI−, APCI+ method) corresponding to MilliQ water quality.

Accordingly, the use of Millistak+® CR40 device for the extractable/leachable removal after single-use assembly use leads to almost full extractable/leachable removal.

Application of Activated Carbon and Clarisolve Filters for the Single-Use Bioprocessing Assemblies (Mobius® Chromatography Assembly)

Figure 9:
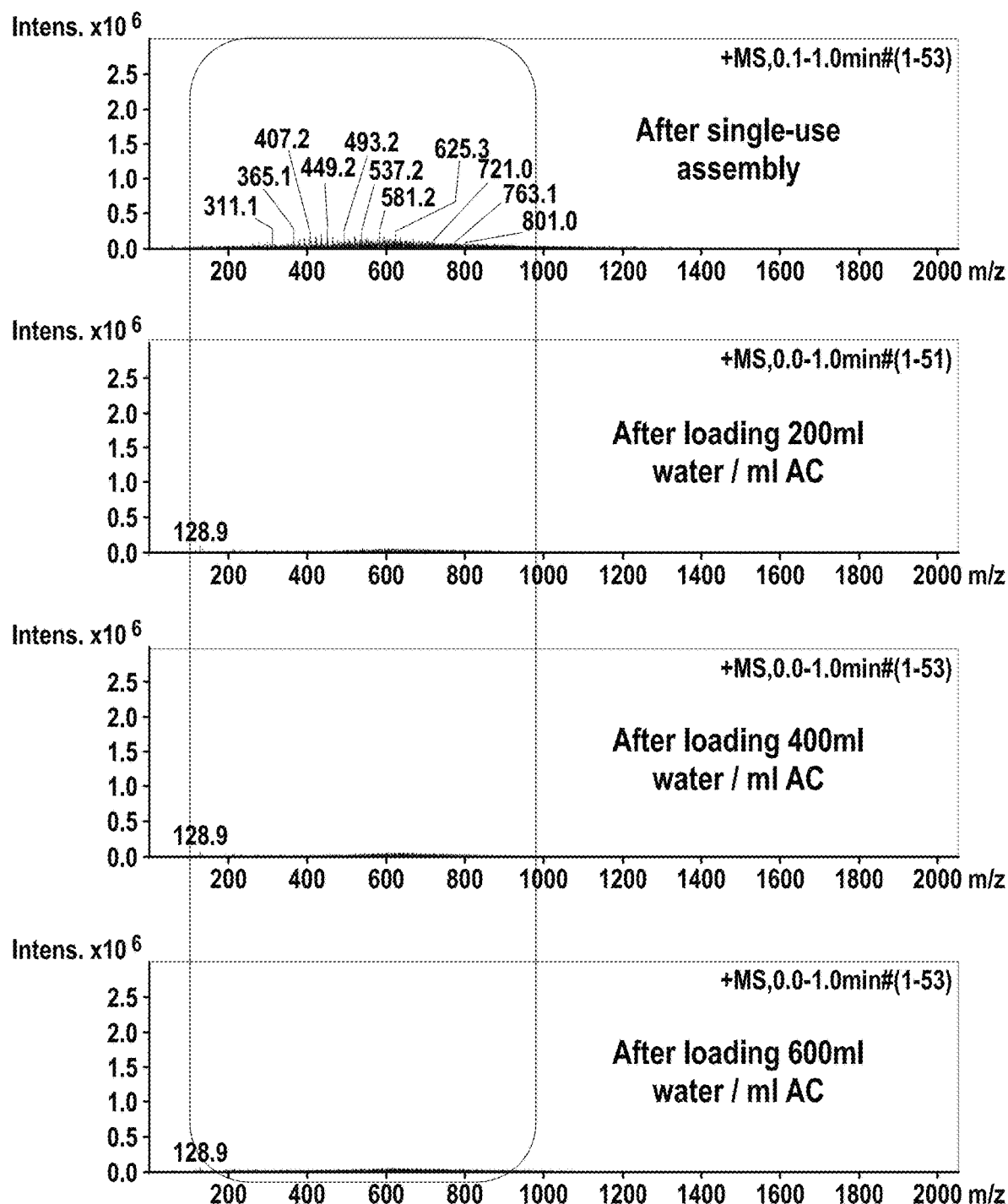
FIG. 9 shows mass spectroscopy results using electrospray ionization (ESI+) method for the extractable/leachable detection after single-use assembly and after loading the processed water on the glass column packed with activated carbon.

For the following example single-use assembly was tested with pure water: Mobius® Disposable Assembly (Gamma Irradiated (min 25-40 kGy; TF20020LGE1, EMD Millipore Corporation, Billerica, Mass., USA) of 20 L solution bag was connected with Lynx ST connector (STC21THN01, EMD Millipore Corporation, Billerica, Mass., USA) to tubing (Pharma 50, 7486040801 PU-6, EMD Millipore Corporation, Billerica, Mass., USA) following by Smart Flexware® Assembly for Chromatography (EMD Millipore Corporation, Billerica, Mass., USA) with Optical XL 600 filter having SHC membrane (EMD Millipore Corporation, Billerica, Mass., USA) connected with female lure (5621000821, EMD Millipore Corporation, Billerica, Mass., USA) to Mobius® Disposable Assembly (Gamma Irradiated (min 25-40 kGy; TF20020LGE1, EMD Millipore Corporation, Billerica, Mass., USA) of 20 L solution bag;

The assembly was installed in a Mobius® Chromatography unit (EMD Millipore Corporation, Billerica, Mass., USA) and 20 L of pure water was flown through using unit's peristaltic pump at 2 L/hour flow rate. The processed water was gathered in the Mobius® Disposable Assembly 20 L solution bag at room temperature. Then the 20 L water containing bag was connected to a equilibrated Superformance® glass column (10*150 mm, Götec Labortechnik, Bickenbach, Germany) packed with activated carbon (100772, Blücher GmbH, Erkrath) and operated at 4 ml/min using peristaltic pump. The flow through water was gathered in separate glass containers and subjected to FIA-MS (flow injection mass spectrometry at 200 µl/min Bruker Esquire 3000+, Bruker Corporation, Billerica, Mass., USA) using electrospray ionization (ESI+) method. The results are given in FIG. 9. Filtration of single-use assembly processed water through glass column packed with activated carbon reduced the level of extractable/leachable (according FIA-MS-ESI+ method) to <ppm range, showing no break through profile.

Then the 20 L water containing bag was connected to a equilibrated Millistak+® media in uPOD™ format CR40 23 cm² (EMD Millipore Corporation, Billerica, Mass., USA) containing activated carbon and operated at 4 ml/min using peristaltic pump. The flow through water was gathered in separate glass containers and subjected to FIA-MS (flow injection mass spectrometry at 200 µl/min Bruker Esquire 3000+, Bruker Corporation, Billerica, Mass., USA) using electrospray ionization (ESI+, ESI−) and atmospheric pressure chemical ionization (APCI−, APCI+) methods. The results are given in FIG. 10-FIG. 13.

Filtration of single-use assembly processed water through Millistak+® CR40 filter reduced the level of extractable/leachable (according FIA-MS-ESI+; ESI− method) by intensity of 10×.

Filtration of single-use assembly processed water through Millistak+® CR40 filter reduced the level of extractable/ leachable (according FIA-MS-APCI−, APCI+ method) corresponding to MilliQ water quality.

Accordingly, the use of Millistak+® CR40 device for the extractable/leachable removal after single-use assembly use leads to almost full extractable/leachable removal.

The invention claimed is:

1. A method for purifying a target molecule comprising:
    separating a target molecule from leachables and/or extractables by contacting a liquid comprising the target molecule and leachables and/or extractables with activated carbon, wherein said leachables and/or extractables are removed from said liquid by said activated carbon,
    wherein said target molecule is a protein with a molecular weight of 10,000 or more, and
    wherein the activated carbon is an activated carbon obtained by pyrolysis of a synthetic, chemically defined organic polymeric material.

2. The method according to claim 1, wherein said target molecule is a glycoprotein.

3. The method according to claim 1, wherein said target molecule is an antibody.

4. The method according to claim 1, wherein the leachables and/or extractables are one or more of the following components: Acetaldehyde, Toluene, 2-Hexanone, Acetone, 2-Butanone, Ethyl Acetate, Bisphenol A, Benzyl alcohol, Trimethyl Silanol, Formaldehyde, Bis (2-ethylhexyl) phthalate, 1-Methylethyl ester acetic acid, 2,4-di-t-butyl Phenol, 2-Octanone, 2-Pentanone, 3,3-dimethyl-2-Butanone, 3-ethoxy-Propane, 3-Hexanone, 3-Methoxy-1-butanol, Butanal, Cyclohexanone, Ethanol, formic acid, Heptaethylene glycol, Hexanal, Methyl isobutyl ketone, Pentanal, t-Butanol, Tetrahydrofuran, Methyl formate.

5. The method according to claim 1, wherein the contact of the target molecule with the activated carbon is carried out at a pH between 3 to 9.

6. The method according to claim 1, wherein the activated carbon has a medium particle size between 5 and 40 μm.

7. The method according to claim 1, wherein the target molecule is separated from leachables and/or extractables by filtration through one or more filters comprising said activated carbon.

8. The method according to claim 1, wherein said method is used hit a production and/or purification process comprising one or more of the following steps:
    Cell culture in a bioreactor,
    Clarification,
    Chromatographic purification, and
    Filtration.

9. The method according to claim 1, wherein the target molecule is contacted with the activated carbon after a process step in which disposable equipment is used in combination with a temperature above 25° C. and/or mechanical deformation of the disposable equipment and/or in which the residence time of the target molecule in the disposable equipment is more than 1 hour.

10. The method according to claim 1, wherein the liquid is contacted with the activated carbon in a filtration device.

11. The method according to claim 1, wherein the activated carbon has a surface area of 10 to 10 000 m$^2$/g.

12. The method according to claim 1, wherein the activated carbon has a surface area of 100 to 5000 m$^2$/g.

13. The method according to claim 1, wherein the activated carbon has a surface area of 1000 to 2000 m$^2$/g.

14. The method according to claim 1, wherein the proportion of activated carbon having a particle size range of 5 to 40 μm is at least 90% by weight.

15. The method according to claim 1, wherein the proportion of activated carbon having a particle size range of 5 to 40 μm is at least 95% by weight.

16. The method according to claim 1, wherein the proportion of activated carbon having a particle size range of 5 to 40 μm is at least 98% by weight.

17. The method according to claim 1, wherein the organic polymeric material is polystyrene, polyamide, polycarbonate, polymethylpentene, polyethylene, polyester, polyvinyl or polypropylene.

18. The method according to claim 1, wherein the organic polymeric material is polystyrene.

19. A method for purifying a target molecule comprising:
    separating a target molecule from leachables and/or extractables by contacting a liquid comprising the target molecule and leachables and/or extractables with activated carbon, wherein said leachables and/or extractables are removed from said liquid by said activated carbon,
    wherein said leachables and/or extractables are impurities within said liquid that result from equipment employed in a production or purification process,
    wherein said target molecule is a protein with a molecular weight of 10,000 or more, and
    wherein the activated carbon is an activated carbon obtained by pyrolysis of a synthetic, chemically defined organic polymeric material.

20. The method according to claim 19, wherein said leachables and/or extractables result from use of disposable equipment in a production or purification process.

* * * * *